US010226197B2

(12) United States Patent
Reinke et al.

(10) Patent No.: US 10,226,197 B2
(45) Date of Patent: Mar. 12, 2019

(54) PACE PULSE DETECTOR FOR AN IMPLANTABLE MEDICAL DEVICE

(71) Applicant: Medtronic, Inc., Minneapolis, MN (US)

(72) Inventors: James D. Reinke, Maple Grove, MN (US); Xusheng Zhang, Shoreview, MN (US); Vinod Sharma, Maple Grove, MN (US); Vladimir P. Nikolski, Blaine, MN (US); Michael B. Terry, Camas, WA (US); Scott A. Hareland, Lino Lakes, MN (US); Daniel L. Hansen, Castle Rock, CO (US); Donna M. Salmi, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 776 days.

(21) Appl. No.: 14/687,053

(22) Filed: Apr. 15, 2015

(65) Prior Publication Data

US 2015/0305642 A1 Oct. 29, 2015

Related U.S. Application Data

(60) Provisional application No. 61/984,249, filed on Apr. 25, 2014.

(51) Int. Cl.
*A61B 5/04* (2006.01)
*A61B 5/0464* (2006.01)
(Continued)

(52) U.S. Cl.
CPC ........ *A61B 5/0464* (2013.01); *A61B 5/04017* (2013.01); *A61B 5/686* (2013.01); *A61N 1/371* (2013.01); *A61N 1/3962* (2013.01)

(58) Field of Classification Search
CPC ... A61B 5/0464; A61B 5/686; A61B 5/04017; A61N 1/371; A61N 1/3962;
(Continued)

(56) References Cited

U.S. PATENT DOCUMENTS

| 4,226,245 A | 10/1980 | Bennett, Jr. |
| 4,328,807 A | 5/1982 | Jirak et al. |

(Continued)

FOREIGN PATENT DOCUMENTS

| CN | 103736206 A | 4/2014 |
| EP | 09239630 | 6/1999 |

(Continued)

OTHER PUBLICATIONS (PCT/US2015/026107) Annex to Form PCT/ISA/206; Communication Relating to the Results of the Partial International Search, dated Jun. 19, 2015, 2 pages.

(Continued)

*Primary Examiner* — Mallika D Fairchild

(57) ABSTRACT

In situations in which an implantable medical device (e.g., a subcutaneous ICD) is co-implanted with a leadless pacing device (LPD), it may be important that the subcutaneous ICD knows when the LPD is delivering pacing, such as anti-tachycardia pacing (ATP). Techniques are described herein for detecting, with the ICD and based on the sensed electrical signal, pacing pulses and adjusting operation to account for the detected pulses, e.g., blanking the sensed electrical signal or modifying a tachyarrhythmia detection algorithm. In one example, the ICD includes a first pace pulse detector configured to obtain a sensed electrical signal and analyze the sensed electrical signal to detect a first type of pulses having a first set of characteristics and a second pace pulse detector configured to obtain the sensed electrical
(Continued)

signal and analyze the sensed electrical signal to detect a second type of pulses having a second set of characteristics.

21 Claims, 13 Drawing Sheets

(51) Int. Cl.
*A61B 5/00* (2006.01)
*A61N 1/37* (2006.01)
*A61N 1/39* (2006.01)

(58) Field of Classification Search
CPC .............. A61N 1/3621; A61N 1/37264; A61N 1/3756; A61N 1/3987; A61N 1/37288
See application file for complete search history.

(56) References Cited

U.S. PATENT DOCUMENTS

| | | |
|---|---|---|
| 4,539,999 A | 9/1985 | Mans |
| 4,664,116 A | 5/1987 | Shaya et al. |
| 4,787,389 A | 11/1988 | Tarjan |
| 4,832,041 A | 5/1989 | Wang et al. |
| 5,010,888 A | 4/1991 | Hossein et al. |
| 5,127,401 A | 7/1992 | Grevious et al. |
| 5,331,966 A | 7/1994 | Bennett et al. |
| 5,448,997 A | 9/1995 | Kruse et al. |
| 5,660,184 A | 8/1997 | Donehoo et al. |
| 5,682,902 A | 11/1997 | Herleikson |
| 5,772,692 A | 6/1998 | Armstrong |
| 5,776,167 A | 7/1998 | Levine et al. |
| 5,913,828 A | 6/1999 | Russell |
| 5,951,483 A | 9/1999 | Joo |
| 6,721,597 B1 | 4/2004 | Bardy et al. |
| 6,754,528 B2 | 6/2004 | Bardy et al. |
| 6,819,953 B2 | 11/2004 | Yonce et al. |
| 6,834,204 B2 | 12/2004 | Ostroff et al. |
| 6,856,835 B2 | 2/2005 | Bardy et al. |
| 6,937,907 B2 | 8/2005 | Bardy et al. |
| 6,952,610 B2 | 10/2005 | Ostroff et al. |
| 6,988,003 B2 | 1/2006 | Bardy et al. |
| 7,027,858 B2 | 4/2006 | Cao et al. |
| 7,043,299 B2 | 5/2006 | Erlinger et al. |
| 7,065,410 B2 | 6/2006 | Bardy et al. |
| 7,069,080 B2 | 6/2006 | Bardy et al. |
| 7,076,294 B2 | 7/2006 | Bardy et al. |
| 7,076,296 B2 | 7/2006 | Rissmann et al. |
| 7,090,682 B2 | 8/2006 | Sanders et al. |
| 7,092,754 B2 | 8/2006 | Bardy et al. |
| 7,146,212 B2 | 12/2006 | Bardy et al. |
| 7,149,575 B2 | 12/2006 | Ostroff et al. |
| 7,181,274 B2 | 2/2007 | Rissmann et al. |
| 7,194,302 B2 | 3/2007 | Bardy et al. |
| 7,239,925 B2 | 7/2007 | Bardy et al. |
| 7,248,921 B2 | 7/2007 | Palreddy et al. |
| 7,274,962 B2 | 9/2007 | Bardy et al. |
| 7,277,754 B2 | 10/2007 | McCabe et al. |
| 7,299,092 B2 | 11/2007 | Bardy et al. |
| 7,299,097 B2 | 11/2007 | Bardy et al. |
| 7,302,300 B2 | 11/2007 | Bardy et al. |
| 7,330,757 B2 | 2/2008 | Ostroff et al. |
| 7,349,736 B2 | 3/2008 | Ostroff et al. |
| 7,376,458 B2 | 5/2008 | Palreddy et al. |
| 7,379,772 B2 | 5/2008 | Bardy et al. |
| 7,392,085 B2 | 6/2008 | Warren et al. |
| 7,406,350 B2 | 7/2008 | Erlinger et al. |
| 7,444,182 B2 | 10/2008 | Ostroff et al. |
| 7,463,924 B2 | 12/2008 | Bardy et al. |
| 7,471,977 B2 | 12/2008 | Zinser, Jr. et al. |
| 7,477,935 B2 | 1/2009 | Palreddy et al. |
| 7,502,645 B2 | 3/2009 | Ostroff et al. |
| 7,536,222 B2 | 5/2009 | Bardy et al. |
| 7,623,909 B2 | 11/2009 | Sanghera et al. |
| 7,623,913 B2 | 11/2009 | Phillips |
| 7,627,367 B2 | 12/2009 | Warren et al. |
| 7,627,375 B2 | 12/2009 | Bardy et al. |
| 7,655,014 B2 | 2/2010 | Ko et al. |
| 7,657,311 B2 | 2/2010 | Bardy et al. |
| 7,657,322 B2 | 2/2010 | Bardy et al. |
| 7,720,534 B2 | 5/2010 | Bardy et al. |
| 7,720,536 B2 | 5/2010 | Rissman et al. |
| 7,751,885 B2 | 7/2010 | Bardy et al. |
| 7,761,150 B2 | 7/2010 | Ghanem et al. |
| 7,774,058 B2 | 8/2010 | Ostroff et al. |
| 7,774,059 B2 | 8/2010 | Ostroff et al. |
| 7,783,340 B2 | 8/2010 | Sanghera et al. |
| 7,835,790 B2 | 11/2010 | Ostroff et al. |
| 7,894,894 B2 | 2/2011 | Stadler et al. |
| 7,953,489 B2 | 5/2011 | Warren et al. |
| 7,991,459 B2 | 8/2011 | Palreddy et al. |
| 7,991,467 B2 | 8/2011 | Markowitz et al. |
| 7,996,082 B2 | 8/2011 | Palreddy et al. |
| 7,996,087 B2 | 8/2011 | Cowan et al. |
| 8,014,851 B2 | 9/2011 | Ostroff et al. |
| 8,014,862 B2 | 9/2011 | Ostroff et al. |
| 8,027,720 B2 | 9/2011 | Bardy et al. |
| 8,050,754 B2 | 11/2011 | Ostroff et al. |
| 8,073,532 B2 | 12/2011 | Palreddy et al. |
| 8,090,438 B2 | 1/2012 | Bardy et al. |
| 8,116,867 B2 | 2/2012 | Ostroff |
| 8,145,305 B2 | 3/2012 | Ostroff et al. |
| 8,157,813 B2 | 4/2012 | Ko et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,185,198 B2 | 5/2012 | Palreddy et al. |
| 8,200,341 B2 | 6/2012 | Sanghera et al. |
| 8,229,563 B2 | 7/2012 | Warren et al. |
| 8,244,349 B2 | 8/2012 | Sanghera et al. |
| 8,249,702 B2 | 8/2012 | Warren et al. |
| 8,265,737 B2 | 9/2012 | Warren et al. |
| 8,265,749 B2 | 9/2012 | Allavatam et al. |
| 8,285,375 B2 | 10/2012 | Bardy et al. |
| 8,346,357 B2 | 1/2013 | Palreddy et al. |
| 8,364,251 B2 | 1/2013 | Phillips |
| 8,386,037 B2 | 2/2013 | Ostroff et al. |
| 8,391,990 B2 | 3/2013 | Smith et al. |
| 8,412,320 B2 | 4/2013 | Ostroff et al. |
| 8,437,838 B2 | 5/2013 | Warren et al. |
| 8,447,398 B2 | 5/2013 | Bardy et al. |
| 8,457,737 B2 | 6/2013 | Bardy et al. |
| 8,457,742 B2 | 6/2013 | Jacobson |
| 8,483,841 B2 | 7/2013 | Sanghera et al. |
| 8,483,843 B2 | 7/2013 | Sanghera et al. |
| 8,494,630 B2 | 7/2013 | Palreddy et al. |
| 8,548,573 B2 | 10/2013 | Keefe |
| 8,565,878 B2 | 10/2013 | Allavatam et al. |
| 8,577,454 B2 | 11/2013 | Bardy et al. |
| 8,588,895 B2 | 11/2013 | Sanghera et al. |
| 8,588,896 B2 | 11/2013 | Allavatam et al. |
| 8,600,489 B2 | 12/2013 | Warren et al. |
| 8,626,280 B2 | 1/2014 | Allavatam et al. |
| 8,626,285 B2 | 1/2014 | Palreddy et al. |
| 8,644,926 B2 | 2/2014 | Ostroff et al. |
| 8,660,668 B2 | 2/2014 | Bardy et al. |
| 8,666,489 B2 | 3/2014 | Ostroff |
| 8,670,826 B2 | 3/2014 | Warren et al. |
| 8,700,152 B2 | 4/2014 | Palreddy et al. |
| 8,712,523 B2 | 4/2014 | Sanghera et al. |
| 8,718,760 B2 | 5/2014 | Bardy et al. |
| 8,718,793 B2 | 5/2014 | O'Connor |
| 8,744,555 B2 | 6/2014 | Allavatam et al. |
| 8,744,572 B1 | 6/2014 | Greenhut et al. |
| 8,750,989 B2 | 6/2014 | Bardy et al. |
| 8,781,567 B2 | 7/2014 | Phillips |
| 8,781,602 B2 | 7/2014 | Sanghera et al. |
| 8,788,023 B2 | 7/2014 | Sanghera et al. |
| 8,801,729 B2 | 8/2014 | Ko et al. |
| 8,825,157 B2 | 9/2014 | Warren et al. |
| 8,831,711 B2 | 9/2014 | Freer et al. |
| 8,831,720 B2 | 9/2014 | Bardy et al. |
| 8,838,234 B2 | 9/2014 | Ostroff et al. |
| 8,855,780 B2 | 10/2014 | Hansen et al. |
| 8,880,161 B2 | 11/2014 | Warren et al. |

(56) References Cited

U.S. PATENT DOCUMENTS

| | | |
|---|---|---|
| 2002/0035379 A1 | 3/2002 | Bardy et al. |
| 2002/0095184 A1 | 7/2002 | Bardy et al. |
| 2002/0107544 A1 | 8/2002 | Ostroff et al. |
| 2004/0230128 A1 | 11/2004 | Brockway et al. |
| 2005/0049643 A9 | 3/2005 | Rissmann et al. |
| 2005/0096703 A1 | 5/2005 | Sanders |
| 2005/0107835 A1 | 5/2005 | Bardy et al. |
| 2006/0173498 A1 | 8/2006 | Banville et al. |
| 2006/0206151 A1 | 9/2006 | Lu |
| 2006/0241700 A1 | 10/2006 | Ghanem et al. |
| 2007/0232944 A1 | 2/2007 | Inagaki |
| 2007/0055314 A1 | 3/2007 | Bardy et al. |
| 2007/0088394 A1 | 4/2007 | Jacobson |
| 2007/0135851 A1 | 6/2007 | Gilkerson et al. |
| 2007/0232948 A1 | 10/2007 | Stadler et al. |
| 2007/0233196 A1 | 10/2007 | Stadler et al. |
| 2007/0233198 A1 | 10/2007 | Ghanem et al. |
| 2007/0239044 A1 | 10/2007 | Ghanem et al. |
| 2007/0239045 A1 | 10/2007 | Ghanem et al. |
| 2007/0239046 A1 | 10/2007 | Ghanem et al. |
| 2007/0239047 A1 | 10/2007 | Ghanem et al. |
| 2007/0239048 A1 | 10/2007 | Ghanem et al. |
| 2007/0239049 A1 | 10/2007 | Ghanem et al. |
| 2007/0239050 A1 | 10/2007 | Ghanem et al. |
| 2007/0239051 A1 | 10/2007 | Ghanem et al. |
| 2007/0270704 A1 | 11/2007 | Ghanem et al. |
| 2007/0276452 A1 | 11/2007 | Sanghera et al. |
| 2008/0103535 A1 | 5/2008 | Ostroff et al. |
| 2008/0132965 A1 | 6/2008 | Ostroff et al. |
| 2008/0272216 A1 | 11/2008 | Kraft et al. |
| 2008/0275517 A1 | 11/2008 | Ghanem et al. |
| 2008/0275518 A1 | 11/2008 | Ghanem et al. |
| 2008/0275519 A1 | 11/2008 | Ghanem et al. |
| 2010/0030093 A1 | 2/2010 | Zhang et al. |
| 2010/0069986 A1 | 3/2010 | Stahl et al. |
| 2010/0114208 A1 | 5/2010 | Donofrio et al. |
| 2010/0152799 A1 | 6/2010 | Sanghera et al. |
| 2010/0331904 A1 | 12/2010 | Warren et al. |
| 2011/0137360 A1 | 6/2011 | Ternes et al. |
| 2011/0307024 A1 | 12/2011 | Ostroff et al. |
| 2012/0029335 A1 | 2/2012 | Sudam et al. |
| 2012/0053477 A1 | 3/2012 | Zhang et al. |
| 2012/0095520 A1 | 4/2012 | Zhang et al. |
| 2012/0197147 A1 | 8/2012 | Allavatam et al. |
| 2012/0271185 A1 | 10/2012 | Sanghera et al. |
| 2012/0316612 A1 | 12/2012 | Warren et al. |
| 2012/0316613 A1 | 12/2012 | Keefe et al. |
| 2013/0053908 A1 | 2/2013 | Smith et al. |
| 2013/0103109 A1 | 4/2013 | Jacobson et al. |
| 2013/0138170 A1 | 5/2013 | Ternes et al. |
| 2013/0268013 A1 | 10/2013 | Sanghera et al. |
| 2014/0046204 A1 | 2/2014 | Allavatam et al. |
| 2014/0046206 A1 | 2/2014 | Sanghera et al. |
| 2014/0046394 A1 | 2/2014 | Allavatam et al. |
| 2014/0094868 A1 | 4/2014 | Allavatam et al. |
| 2014/0172032 A1 | 6/2014 | Palreddy et al. |
| 2014/0200592 A1 | 7/2014 | O'Connor |
| 2014/0214104 A1 | 7/2014 | Greenhut et al. |
| 2014/0221857 A1 | 8/2014 | Allavatam et al. |
| 2014/0222097 A1 | 8/2014 | Bardy et al. |
| 2014/0257120 A1 | 9/2014 | Warren et al. |
| 2014/0257421 A1 | 9/2014 | Sanghera et al. |
| 2014/0275917 A1 | 9/2014 | Allavatam et al. |
| 2014/0276155 A1 | 9/2014 | Zhang |
| 2014/0276158 A1 | 9/2014 | Zhang |
| 2014/0276159 A1 | 9/2014 | Zhang |
| 2014/0276160 A1 | 9/2014 | Zhang et al. |
| 2014/0296932 A1 | 10/2014 | Sanghera et al. |
| 2014/0324068 A1 | 10/2014 | Ko et al. |

FOREIGN PATENT DOCUMENTS

| | | |
|---|---|---|
| JP | 60222068 | 11/1985 |
| JP | 10165383 | 6/1998 |
| WO | 2012011065 A1 | 1/2012 |

OTHER PUBLICATIONS

Zhang, "Method and Apparatus for Discriminating Tachycardia Events in a Medical Device Using Two Sensing Vectors", U.S. Appl. No. 14/250,040, filed Apr. 10, 2014, 52 pages.

(PCT/US2015/026107) PCT Notification of Transmittal of the International Search Report and the Written Opinion of the International Searching Authority, dated Aug. 26, 2015, 19 pages.

Reinke et al, "Pace Pulse Detector for an Implantable Medical Device" Japanese Office Action for JP Application No. 2017-507682, dated Nov. 19, 2018, in Japanese, 4 pages.

Reinke et al, "Pace Pulse Detector for an Implantable Medical Device" Japanese Office Action for JP Application No. 2017-507682, dated Nov. 19, 2018, English translation, 3 pages.

PACE PULSE DETECTOR FOR AN IMPLANTABLE MEDICAL DEVICE

This application claims the benefit of U.S. Provisional Application No. 61/984,249, filed on Apr. 25, 2014, the content of which is incorporated herein by reference in its entirety.

TECHNICAL FIELD

This application relates to medical devices, and, more particularly, to implantable medical devices configured to detect and treat cardiac arrhythmias.

BACKGROUND

ICD systems may be used to deliver high energy cardioversion or defibrillation shocks to a patient's heart to terminate a detected tachyarrhythmia, such as an atrial or ventricular fibrillation. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by the ICD. Additionally, ICD systems may also deliver high energy cardioversion or defibrillation shocks to terminate certain types of ventricular tachycardia (VT).

ICD systems generally include an ICD that is coupled to one or more electrical leads placed within or attached to the heart. The electrical leads include one or more electrodes positioned in or on the heart by the leads and used for therapy and/or sensing functions. Cardioversion and defibrillation shocks (e.g., anti-tachyarrhythmia or high voltage shocks) are generally applied between a coil electrode carried by one of the leads and the ICD housing, which acts as an active can electrode.

In addition, or as an alternative to cardioversion and defibrillation shocks, the ICD system may provide pacing therapy to the heart. Conventional ICD systems provide the pacing therapy via the electrodes of the lead that are positioned near or against the cardiac tissue to provide sufficient transmission of electrical energy to the cardiac tissue in order to capture the heart. The pacing therapy may, for example, include cardiac pacing to suppress or convert tachyarrhythmias to sinus rhythm. Such pacing is often referred to as anti-tachycardia pacing or ATP. The ICD system may provide ATP in an attempt to terminate arrhythmias that would otherwise need to be treated by a cardioversion or defibrillation shock, which are uncomfortable for the patient. The ICD system may also provide anti-bradycardia pacing when the natural pacemaker and/or conduction system of the heart fails to provide synchronized atrial and ventricular contractions at rates and intervals sufficient to sustain healthy patient function.

SUMMARY

Subcutaneous ICD systems have also been developed that do not include leads that are within or attached to the heart. In a subcutaneous ICD system, the lead is instead placed subcutaneously above the ribcage and/or sternum. Such systems do not generally provide ATP because of the amount of energy required for such pacing pulses as well as the discomfort experienced by the subject in which the device is implanted. Systems have been proposed in which a leadless pacing device (LPD) or other artificial pacemaker is implanted along with the subcutaneous ICD to provide the desired ATP.

In situations in which a subcutaneous ICD operates in conjunction with a co-implanted LPD it may be important that the subcutaneous ICD knows when pacing, such as ATP, is being or has been delivered by the LPD. Based on the knowledge that pacing is being or has been delivered, the subcutaneous ICD may make some sort of adjustment to account for the pacing. For example, the subcutaneous ICD may blank the sensing channel to remove the pacing pulse from the sensed electrical signal, adjust a tachyarrhythmia detection algorithm, make another adjustment, or a combination thereof.

In one example, this disclosure is directed to an implantable medical device comprising a first pace pulse detector configured to obtain a sensed electrical signal and analyze the sensed electrical signal to detect a first type of pulses having a first set of characteristics and a second pace pulse detector configured to obtain the sensed electrical signal and analyze the sensed electrical signal to detect a second type of pulses having a second set of characteristics.

In another example, this disclosure provides a method comprising processing electrical signals sensed on an implantable electrical lead coupled to an implantable medical device, detecting, based on the processing of the electrical signals sensed on the implantable electrical lead, delivery of pacing pulses from a second implantable medical device, wherein the detecting comprises detecting a first type of pulse having a first set of characteristics and a second type of pulse having a second set of characteristics different than the first set, modifying the sensed electrical signal to remove the first type of pulse from the sensed electrical signal, and modifying a tachyarrhythmia detection algorithm based on the detected pacing pulses.

In a further example, this disclosure is directed to an extravascular implantable cardioverter-defibrillator (ICD) comprising a sensing module that obtains electrical signals sensed using at least an implantable electrical lead coupled to the ICD, a pace detector including a first pace pulse detector that detects, within the obtained electrical signals, a first type of pulses having a first set of characteristics and a second pace pulse detector that detects, within the obtained electrical signals, a second type of pulses having a second set of characteristics different than the first set of characteristics, a blanking module that holds the sensed electrical signal at a current value to remove the first type of pulse from the sensed electrical signal, and a control module that modifies a tachyarrhythmia detection algorithm based on the detected pacing pulses.

The details of one or more examples are set forth in the accompanying drawings and the description below. Other features, objects, and advantages will be apparent from the description and drawings, and from the claims.

DETAILED DESCRIPTION

Figure 1:
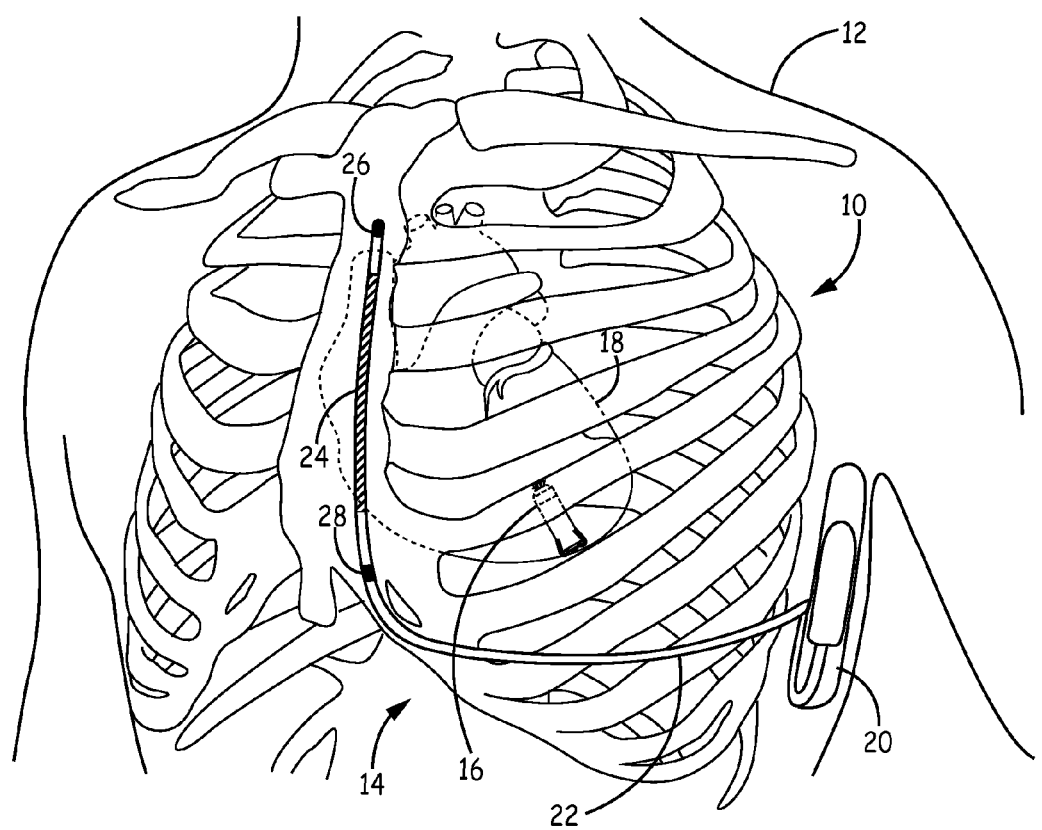
FIG. 1 is a conceptual drawing illustrating an example cardiac system having coexistent ICD system and pacing system implanted within a patient.

FIG. 1 is a conceptual drawing illustrating an example cardiac system 10 implanted within a patient 12. Cardiac system 10 includes a subcutaneous ICD system 14 implanted above the ribcage and sternum and a leadless cardiac pacing device 16 implanted within a heart 18 of patient 12. As will be described in further detail herein, subcutaneous ICD system 14 is configured to detect pacing therapy delivered by pacing device 16 by analyzing sensed electrical signals and, in response to detecting the pacing therapy, modify sensing and/or tachyarrhythmia detection.

Subcutaneous ICD system 14 includes an implantable cardiac defibrillator (ICD) 20 connected to at least one implantable cardiac defibrillation lead 22. ICD 20 of FIG. 1 is implanted subcutaneously on the left side of patient 12 under the skin but above the ribcage. Defibrillation lead 22 extends subcutaneously under the skin but above the ribcage from ICD 20 toward a center of the torso of patient 12, bends or turns near the center of the torso, and extends subcutaneously superior under the skin but above the ribcage and/or sternum. Defibrillation lead 22 may be offset laterally to the left or the right of the sternum or located over the sternum. Defibrillation lead 22 may extend substantially parallel to the sternum or be angled lateral from the sternum at either the proximal or distal end.

Defibrillation lead 22 includes an insulative lead body having a proximal end that includes a connector configured to be connected to ICD 20 and a distal portion that includes one or more electrodes. Defibrillation lead 22 also includes one or more conductors that form an electrically conductive path within the lead body and interconnect the electrical connector and respective ones of the electrodes.

Defibrillation lead 22 includes a defibrillation electrode 24 toward the distal portion of defibrillation lead 22, e.g., toward the portion of defibrillation lead 22 extending along the sternum. Defibrillation lead 22 is placed along sternum such that a therapy vector between defibrillation electrode 24 and a housing electrode formed by or on ICD 20 (or other second electrode of the therapy vector) is substantially across a ventricle of heart 18. The therapy vector may, in one example, be viewed as a line that extends from a point on defibrillation electrode 24 (e.g., a center of the defibrillation electrode 24) to a point on the housing electrode of ICD 20. Defibrillation electrode 24 may, in one example, be an elongated coil electrode.

Defibrillation lead 22 may also include one or more sensing electrodes, such as sensing electrodes 26 and 28, located along the distal portion of defibrillation lead 22. In the example illustrated in FIG. 1, sensing electrodes 26 and 28 are separated from one another by defibrillation electrode 24. In other examples, however, sensing electrodes 26 and 28 may be both distal of defibrillation electrode 24 or both proximal of defibrillation electrode 24. In other examples, lead 22 may include more or fewer electrodes.

ICD system 14 may sense electrical signals via one or more sensing vectors that include combinations of electrodes 26 and 28 and the housing electrode of ICD 20. For example, ICD 20 may obtain electrical signals sensed using a sensing vector between electrodes 26 and 28, obtain electrical signals sensed using a sensing vector between electrode 26 and the conductive housing electrode of ICD 20, obtain electrical signals sensed using a sensing vector between electrode 28 and the conductive housing electrode of ICD 20, or a combination thereof. In some instances, ICD 20 may even sense cardiac electrical signals using a sensing vector that includes defibrillation electrode 24 and one of electrodes 26 and 28 or the housing electrode of ICD 20.

The sensed electrical intrinsic signals may include electrical signals generated by cardiac muscle and indicative of depolarizations and repolarizations of heart 18 at various times during the cardiac cycle. Additionally, the sensed electrical signals may also include electrical signals, e.g., pacing pulses, generated and delivered to heart 18 by pacing device 16. ICD 20 analyzes the electrical signals sensed by the one or more sensing vectors to detect tachyarrhythmia, such as ventricular tachycardia or ventricular fibrillation. In response to detecting the tachycardia, ICD 20 may begin to charge a storage element, such as a bank of one or more capacitors, and, when charged, deliver one or more defibrillation shocks via defibrillation electrode 24 of defibrillation lead 22 if the tachyarrhythmia is still present and determined to require defibrillation therapy. As will be described in further detail herein, ICD 20 analyzes the sensed electrical signals on lead 22 to detect pacing therapy provided by pacing device 16 and, in response to detecting the pacing therapy, modifies the sensing and/or tachyarrhythmia detection to reduce the likelihood that the pacing therapy negatively impacts the sensing and detection of ICD 20.

As described above, cardiac system 10 also includes at least one cardiac pacing device 16. In the example illustrated in FIG. 1, cardiac pacing device 16 is an implantable leadless pacing device that provides pacing therapy to heart 18 via a pair of electrodes carried on the housing of pacing device 16. An example cardiac pacing device is described in U.S. patent application Ser. No. 13/756,085 to Greenhut et al., entitled "SYSTEMS AND METHODS FOR LEADLESS PACING AND SHOCK THERAPY," the entire content of which is incorporated herein by reference. Since cardiac pacing device 16 includes two or more electrodes carried on the exterior its housing, no other leads or structures need to reside in other chambers of heart 18.

In the example of FIG. 1, cardiac pacing device 16 is implanted within right ventricle of heart 18 to sense electrical activity of heart 18 and deliver pacing therapy, e.g., anti-tachycardia pacing (ATP) therapy, bradycardia pacing therapy, and/or post-shock pacing therapy, to heart 18. Pacing device 16 may be attached to a wall of the right ventricle of heart 18 via one or more fixation elements that penetrate the tissue. These fixation elements may secure pacing device 16 to the cardiac tissue and retain an electrode (e.g., a cathode or an anode) in contact with the cardiac tissue. However, in other examples, system 10 may include additional pacing devices 16 within respective chambers of heart 12 (e.g., right or left atrium and/or left ventricle). In further examples, pacing device 16 may be attached to an external surface of heart 18 (e.g., in contact with the epicardium) such that pacing device 16 is disposed outside of heart 18.

Pacing device 16 may be capable sensing electrical signals using the electrodes carried on the housing of pacing device 16. These electrical signals may be electrical signals generated by cardiac muscle and indicative of depolarizations and repolarizations of heart 18 at various times during the cardiac cycle. Pacing device 16 may analyze the sensed electrical signals to detect tachyarrhythmias, such as ventricular tachycardia or ventricular fibrillation. In response to detecting the tachyarrhythmia, pacing device 16 may, e.g., depending on the type of tachyarrhythmia, begin to deliver ATP therapy via the electrodes of pacing device 16. In addition to or instead of ATP therapy, pacing device 16 may also deliver bradycardia pacing therapy and post-shock pacing therapy.

Cardiac pacing device 16 and subcutaneous ICD system 14 are configured to operate completely independent of one another. In other words, pacing device 16 and subcutaneous ICD system 14 are not capable of establishing telemetry communication sessions with one another to exchange information about sensing and/or therapy using one-way or two-way communication. Instead, each of pacing device 16 and subcutaneous ICD system 14 analyze the data sensed via their respective electrodes to make tachyarrhythmia detection and/or therapy decisions. As such, each device does not know if the other will detect the tachyarrhythmia, if or when it will provide therapy, and the like.

During a tachyarrhythmia that could be treated with either ATP or a defibrillation shock, it is important to ensure that ATP therapies do not overlap or take place after the defibrillation shock. Applying ATP after a defibrillation shock could be pro-arrhythmic and present a hazard to the patient. Moreover, the delivery of the pacing from pacing device 16 could interference with sensing and tachyarrhythmia detection of subcutaneous ICD 20. This interference could take the form of decreased sensitivity (e.g., inability to detect ventricular tachycardia (VT) and/or ventricular fibrillation (VF)) or decreased specificity (e.g., inability to withhold therapy for tachyarrhythmia's determined to not require a defibrillation shock, such as supraventricular tachycardia (SVT), sinus tachycardia (ST), normal sinus rhythm, atrial fibrillation, atrial flutter, or the like). Systems could be designed to provide device-to-device communication between subcutaneous ICD system 14 and pacing device 16, but this may add complexity to the system and not be highly effective or fast enough to prevent unwanted ATP therapies post defibrillation shock. The techniques described herein reduce and, in some cases, eliminate the interference with sensing and tachyarrhythmia detection of subcutaneous ICD 20.

Although FIG. 1 is described in the context of a subcutaneous ICD system 14 and a leadless pacing device 16, the techniques may be applicable to other coexistent systems. For example, an ICD system that includes a lead having a distal portion that is implanted at least partially under the sternum (or other extra-pericardial location) instead of being implanted above the ribs and/or sternum. As another example, instead of a leadless pacing device, a pacing system may be implanted having a pacemaker and one or more leads connected to and extending from the pacemaker into one or more chambers of the heart or attached to the outside of the heart to provide pacing therapy to the one or more chambers. Moreover, the techniques of this disclosure may additionally be useful in implantable medical systems that do not include an ICD 20. For example, it may be beneficial for leadless pacing devices implanted in different chambers of the heart to be able to detect pacing pulses delivered by each other so that no direct communication is necessary. As such, the example of FIG. 1 is illustrated for exemplary purposes only and should not be considered limiting of the techniques described herein.

Figure 2:
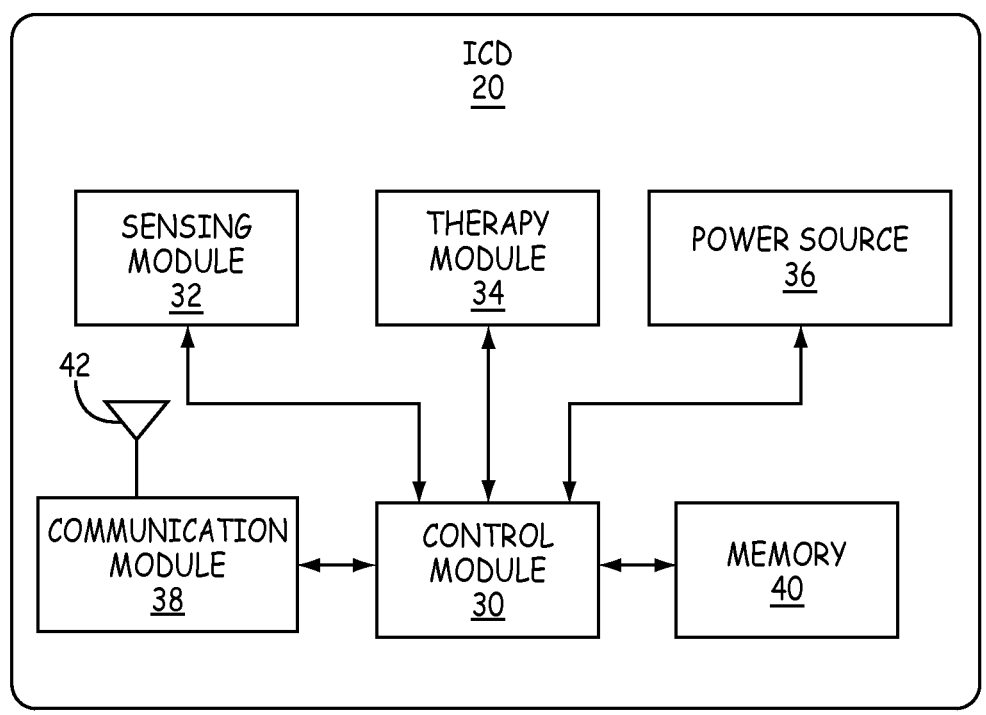
FIG. 2 is a functional block diagram of an example configuration of electronic components of an example ICD.

FIG. 2 is a functional block diagram of an example configuration of electronic components of an example ICD 20. ICD 20 includes a control module 30, sensing module 32, therapy module 34, communication module 38, and memory 40. The electronic components may receive power from a power source 36, which may, for example, be a rechargeable or non-rechargeable battery. In other embodiments, ICD 20 may include more or fewer electronic components. The described modules may be implemented together on a common hardware component or separately as discrete but interoperable hardware, firmware or software components. Depiction of different features as modules is intended to highlight different functional aspects and does not necessarily imply that such modules must be realized by separate hardware, firmware or software components. Rather, functionality associated with one or more modules may be performed by separate hardware, firmware or software components, or integrated within common or separate hardware, firmware or software components.

Sensing module 32 is electrically coupled to some or all of electrodes 24, 26, and 28 via conductors of lead 22 and one or more electrical feedthroughs, and is also electrically coupled to the housing electrode via conductors internal to the housing of ICD 20. Sensing module 32 is configured to obtain electrical signals sensed via one or more combinations of electrodes 24, 26, and 28, and the housing electrode of ICD 20, and process the obtained electrical signals.

Sensing module 32 may include one or more analog components, digital components or a combination thereof. Sensing module 32 may convert the sensed signals to digital form and provide the digital signals to control module 30 for processing or analysis. For example, sensing module 32 may amplify signals from the sensing electrodes and convert the amplified signals to multi-bit digital signals using an analog-to-digital converter (ADC). Sensing module 32 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 30. Sensing module 32 may also process the sensed signals to output an electrocardiogram to control module 30.

Control module 30 may process the signals from sensing module 32 to monitor for a tachyarrhythmia, such as VT or VF. In response to detecting the tachyarrhythmia, control module 30 may control therapy module 34 to charge a storage element within therapy module 34, and, when necessary, deliver a cardioversion or defibrillation pulse to terminate the tachyarrhythmia. The cardioversion or defibrillation pulse may be provided using a therapy vector between defibrillation electrode 24 of lead 22 and the housing electrode of ICD 20. Therapy module 34 may, for example, include one or more capacitors, transformers, switches, and the like. Control module 30 may control therapy module 34 to generate and deliver cardioversion or defibrillation shocks having any of a number of waveform properties, including leading-edge voltage, tilt, delivered energy, pulse phases, and the like.

As described above with respect to FIG. 1, pacing device 16 independently detects a tachyarrhythmia and, in some instances, provides ATP in an attempt to terminate the tachyarrhythmia. The ATP therapy provided by pacing device 16 may interfere with sensing and detection of tachyarrhythmia by sensing module 32 of ICD 20. This interference could take the form of decreased sensitivity (e.g., inability to detect VT or VF) or decreased specificity (e.g., detecting VT or VF for rhythms in which no therapy is necessary). ICD 20 is configured to detect the ATP provided by pacing device 16 by analyzing the sensed electrical signals from lead 22 and, adjust sensing and/or detection in response to detecting the ATP. To this end, sensing module 32 may include additional components configured to detect pacing spikes within the sensed electrical signals from lead 22. For example, sensing module 32 may include a pace pulse detector as described in further detail with respect to FIGS. 3 and 5.

Communication module 38 includes any suitable hardware, firmware, software or any combination thereof for communicating with an external device, such as a clinician programmer or patient monitoring device. For example, communication module 38 may include appropriate modulation, demodulation, frequency conversion, filtering, and amplifier components for transmission and reception of data via antenna 42. Antenna 42 may be located within the connector block of ICD 20 or within housing ICD 20.

The various modules of ICD 20 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 40 may include computer-readable instructions that, when executed by control module 30 or other component of ICD 20, cause one or more components of ICD 20 to perform various functions attributed to those components in this disclosure. Memory 40 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 3:
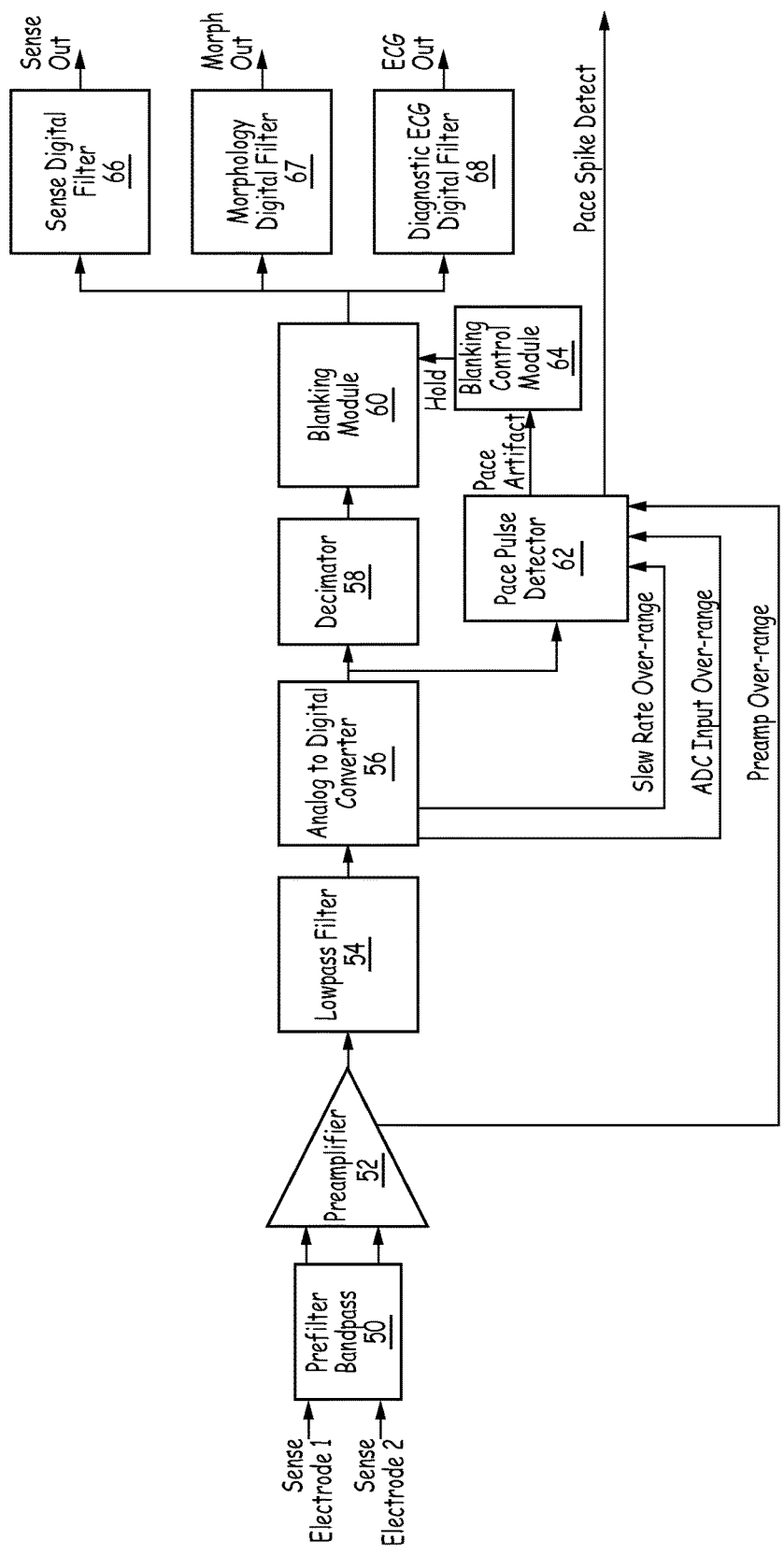
FIG. 3 is a block diagram of an example sensing channel of a sensing module of an ICD with pace detection and removal.

FIG. 3 is a block diagram of an example sensing channel of a sensing module, such as sensing module 32 of FIG. 2 or a sensing module in another implantable medical device (e.g., a leadless pacing device). The sensing channel may, for example, be a sensing channel for processing sensed signals on a first sensing vector. Sensing module 32 may include a similar sensing channel for each of the sensing vectors to be processed. In the case of multiple sensing channels, sensing module 32 may include duplicate components or each sensing channel may share one or more components.

The sensing channel illustrated in FIG. 3 includes a prefilter 50, preamplifier 52, low-pass filter 54, analog-to-digital converter (ADC) 56, decimator 58, blanking module 60, pace pulse detector 62, blanking control module 64, sense digital filter 66, ECG morphology digital filter 67, and ECG filter 68. The configuration of the sensing channel is exemplary in nature and should not be considered limiting of the techniques a described herein. The sensing channel of sensing module 32 may include more or fewer components than illustrated and described in FIG. 3.

The electrical signals sensed on a sensing vector of lead 22 are provided to prefilter 50 of sensing module 32. The electrical signals provided to prefilter 50 are differential signals. Prefilter 50 may include one or more passive resistor-capacitor (RC) band-pass filters and protection diodes to filter out direct current, high frequency, and high voltage transient signals. The prefiltered signal from prefilter 50 is provided to preamplifier 52, which amplifies the input signals by a gain and converts the prefiltered differential signals to a single-ended signal.

Preamplifier 52 may, in some instances, also generate a signal when an input or output level exceeds a range of the preamplifier (labeled "preamp over-range" in FIG. 3). The range of preamplifier may be between ±10-20 millivolts (mV). However, the range may be smaller or larger in other embodiments. Preamplifier 52 may generate the preamp over-range signal when the input signal causes the preamplifier to be over-range. Such a condition may be indicative of an input signal greater than approximately 10-20 mV, which is much larger than the expected amplitude of an electrical signal corresponding to a ventricular contraction, which would be closer to 1-5 mV. The preamp over-range signal is provided to pace pulse detector 62 for analysis in determining whether or not a pace spike or a pace artifact are detected as will be described further below.

The preamplified signal is output by preamplifier 52 to low pass filter 54. Low pass filter 54 may provide anti-alias filtering and noise reduction prior to digitization. The filtered signal output by low pass filter 54 is provided to ADC 56, which converts the analog signal to a digital bit stream. In one example, ADC 56 may be a sigma-delta converter (SDC), but other types of ADCs may be used. The output of ADC 56 is provided to decimator 58, which functions as a digital low-pass filter that increases the resolution and reduces the sampling rate. In one example, ADC may have an 8-bit resolution and 16 kiloHertz (kHz) sampling rate. Decimator 58 may have a 16-bit resolution and a 1 kHz sampling rate. These values are for example purposes only and should not be considered limiting of the techniques described herein. ADC 56 may also have other characteristics, such as an input range and a slew rate range. In one example, the input range of ADC 56 may be between 25-825 mV and the slew rate range may be 0 to 6.24 mV/ms, 3.12 mV/ms, 1.56 mV/ms, or 0.78 mV/ms. ADC 56 may be configured to generate an ADC input over-range signal when the input signal is greater than the input range of ADC 56. Such a condition may, for example, be indicative of a sensed signal greater than approximately 10-20 mV peak which is much larger than an expected ventricular contraction 1-5 mV. Alternatively or additionally, ADC 56 may be configured to generate a slew rate over-range signal when the slew rate is faster than can be tracked by ADC 56. For example, the accumulated voltage error signal internal to ADC 56 may be monitored with a comparator and when the error signal exceeds the comparator threshold, the slew over-range is tripped. The slew-rate overange may, in one instance, may be generated or asserted when the slew rate of the input signal is greater than or equal to 4 mV/ms. The ADC input over-range signal and/or the slew rate over-range signal are provided to pace pulse detector 62 for analysis in determining whether a pace spike or a pace artifact are detected.

In conventional sensing channels, the digitized signal is provided directly to sense filter 66 and ECG filter 68. Sense digital filter 66 includes a bandpass filter (e.g., 10 to 32 Hz), rectifier, and a threshold detector. The sense digital filter 66 may, in one example, include an auto-adjusting threshold that dynamically varies between a percentage of the peak value of the signal input to sense digital filter 66 and a programmed minimum value. The output of sense digital filter 66, which is provided to control module 30, indicates that a cardiac event is detected, e.g., an R-wave in the case of ventricular sensing channel or a P-wave in the case of a atrial sensing channel, whenever the sensed electrical signal exceeds the threshold. In parallel with the processing by sense digital filter 66, diagnostic ECG filter 68 applies a wide bandwidth filter to output an ECG signal and a morphology ECG filter 67 applies a filter (e.g. with a bandwidth of 2.5 to 32 Hz) go output a signal for morphology analysis (including gross-morphology analysis and beat-based morphology analysis described below in further detail) by control module 30.

Figure 4A:
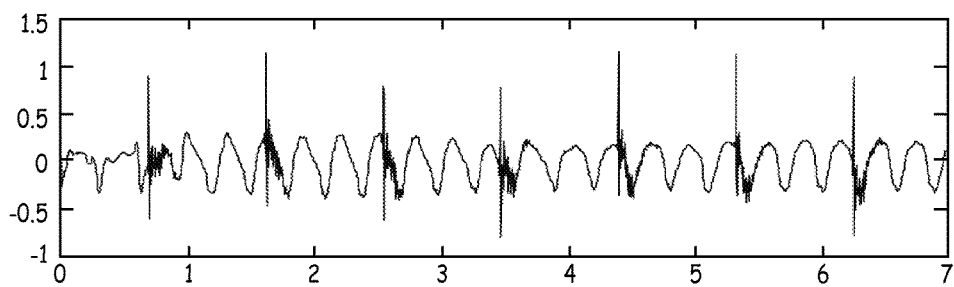
FIG. 4A illustrates a plot of an ECG of a ventricular tachycardia with pacing spikes.
Figure 4B:
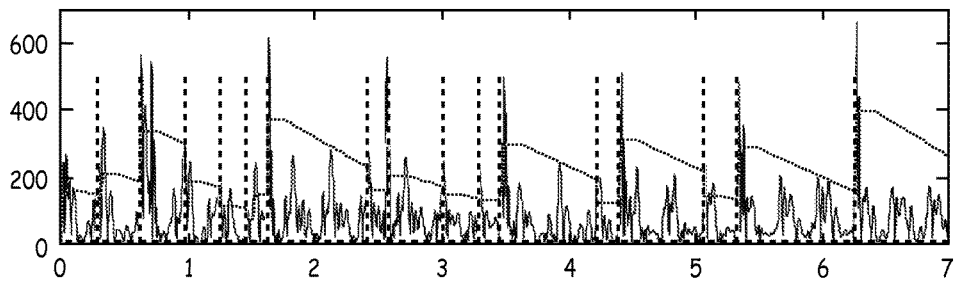
FIG. 4B illustrates a plot representing operations performed on the ECG and occurring within sense digital filter showing the impact of pacing artifacts on sensing performance.

As described above, the pacing pulses delivered by pacing device 16 could interfere with sensing and tachyarrhythmia detection of subcutaneous ICD 20 either by decreasing sensitivity and/or specificity. FIGS. 4A and 4B illustrate example electrical signals in which pacing pulses are delivered on top of a ventricular tachycardia. FIG. 4A illustrates an ECG of the rhythm and FIG. 4B illustrates a plot representing operations occurring within sense digital filter 66. In the plot illustrated in FIG. 4B, the solid line signal is the bandpass filtered and rectified ECG. The dotted line signal is the auto-adjusting sensing threshold of sense digital filter 66, which as described above, may dynamically vary between a percentage of the peak value of the signal input to sense digital filter 66 and a programmed minimum value. When the ECG signal exceeds the auto-adjusting sensing threshold, a sensed event is detected, as indicated by the vertical bold dashed lines. The sense digital filter outputs these detected sensed events to control module 30 for further processing/analysis.

As can be seen from the illustrations of FIGS. 4A and 4B, the large amplitude of the pacing pulses cause the auto adjusting sensing threshold to increase to a value that is too large to detect at least some of the cardiac events of the underlying rhythm subsequent to the pacing pulse. In turn, control module 30 does not have an accurate representation of cardiac events for use in detecting a tachyarrhythmia. The large pacing pulse may also cause artifacts in the ECG signal for a short time after the pacing pulse due to the pacing pulse exceeding the input range of the preamplifier, the input range of the ADC, the slew rate of the ADC, or otherwise affecting a component of the sensing channel.

To account for the possible interference in sensing and tachyarrhythmia detection of ICD 20 caused by the independent pacing therapy provided by pacing device 16, ICD 20 includes pace pulse detector 62, blanking module 60, and blanking control module 64 within the sensing channel(s). Pace pulse detector 62 obtains the signal output by ADC 56 in parallel with decimator 58. Pace pulse detector 62 may include one or more components to process the signal obtained from ADC 56 to identify characteristics of a pacing pulse. In one example, pace pulse detector 62 may process the signal input from ADC 56 to analyze an amplitude of the signal, a slew rate of the signal, and/or a pulse width of the signal. Pace pulse detector 62 may include a filter configured to pass electrical signals corresponding to pacing pulses and reject cardiac electrical signals (e.g., a band-pass filter that passes signals having frequencies between approximately 100 Hz and 2000-4000 Hz, for example or a high-pass filter that passes signals having frequencies greater than 100 Hz). Alternatively or additionally, pace pulse detector 62 may include a differentiator, difference filter, or a first order derivative filter that may be used to obtain a signal representative of the slew rate of the sensed signal.

Pace pulse detector 62 may also include one or more threshold detectors. For example, pace pulse detector may include a slew rate threshold detector that compares the output of a differentiator or a first order derivative filter to a slew rate threshold. If the slew rate exceeds the slew rate threshold, pace pulse detector 62 determines that the signal corresponds to a pacing pulse. Pace pulse detector 62 may likewise analyze the amplitude of the input signal. In some instances, pace pulse detector 62 may analyze a combination of slew rate and amplitude to detect the presence of a pacing pulse. For example, if the slew rate exceeds the slew rate threshold, pace pulse detector 62 may compare the amplitude of the sensed signal to one or more amplitude thresholds using amplitude threshold detectors.

In some instances, pace pulse detector 62 may include a plurality of pace pulse detectors. In one embodiment, pace pulse detector 62 may include two pace pulse detectors. A first detector, e.g., referred to herein as a pace artifact detector, has a first threshold that is configured to detect only pacing pulses having characteristics, e.g., large enough in amplitude, slew rate, and/or pulse width, to impact the sensitivity for tachyarrhythmia detection of ICD 20. Such pacing pulses will be referred to herein as pace artifacts. In one example, the pace artifact detector may be configured to detect pacing pulses having amplitudes that are greater than or equal to 2-10 mV for pulse widths of approximately 1 ms. In another example, the pace artifact detector may configured to detect pacing pulses having amplitudes that are greater than or equal to 4 mV and pulse widths of approximately 1 ms. However, the characteristics of the pacing pulses that the pace artifact detector is configured to detect may be different.

A second detector, e.g., referred to herein as a pace spike detector, has a second threshold that is configured to detect all pacing pulses regardless of whether they are large enough or have other characteristics to impact tachyarrhythmia detection. These pacing pulses will be referred to herein as pace spikes. In one example, the pace spike detector may be configured to detect pacing pulses having amplitudes that are greater than or equal to 1 mV and pulse widths of approximately 1 ms. However, the characteristics of the pacing pulses that the pace spike detector is configured to detect may be different. Although no modifications of the electrical signal will occur for these smaller pacing spikes, control module 30 may still utilize this information in its tachyarrhythmia detection. The pace spike detector will have a higher sensitivity than the pace artifact detector so that it can detect pacing pulses having small amplitudes and/or pulse widths. As such, pace artifacts will also be detected as pace spikes. As such, pace pulse detector 62 may analyze the slew rate, amplitude, pulse width and/or other characteristic to detect pace artifacts and pace spikes.

In further instances, pace pulse detector 62 may include only a single detector or more than two pulse detectors. For example, pace pulse detector 62 may include a third pulse detector to detect noise or determine margin between a peak of the pacing pulse signal (e.g., spike or artifact) and the threshold of one or both of the first and second pulse detectors. An example pace pulse detector 62' that includes three detectors is described below with respect to FIG. 8.

In addition to inputting the signal from ADC 56, pace pulse detector 62 also obtains the preamp over-range signal from preamplifier 52, the ADC input over-range signal from ADC 56, and the slew rate over-range signal from ADC 56. All or at least some of these signals may be indicative of a pacing artifact. For example, a preamplifier over-range signal that is present or asserted for a threshold period of time is likely indicative of a sensed signal that is much larger than an expected ventricular contraction 1-5 mV. As another example, an ADC slew rate over-range signal that is present or asserted for more than a threshold amount of time, e.g., approximately 1 ms, is likely indicative of a pacing artifact as the slew rate limit of ADC 56 would not be exceeded for a very long time for EMI (e.g., less than 1 ms) and never exceeded for sensed ventricular contractions. In some instances, the threshold time may be adjustable. In a further example, an ADC input over-range signal that is present or asserted for more than a threshold amount of time, e.g., about 1 ms, is likely indicative of a sensed signal that is has a high amplitude for much longer than a ventricular contraction. As such, each of these over-range signals may meet particular criteria that is likely indicative of the presence of a pace pulse that is high enough in amplitude and/or pulse width to impact the sensitivity for tachyarrhythmia detection by ICD 20, i.e., a pace artifact. These criteria will be referred to as over-range conditions. In other examples, the simple fact the over-range condition occurs (regardless of how long it occurs for) may be an over-range condition.

Pace pulse detector 62 analyzes these over-range signals as well as the pace spike analysis and/or pace artifact analysis performed as described above and outputs a pace artifact detection signal and a pace spike detection signal based on the analyses. In one example, pace pulse detector 62 generates and/or asserts the pace artifact detect signal when any of the over-range conditions are met or the amplitude, slew rate, and pulse width analysis indicates that the presences of a pacing artifact. Likewise, pace pulse detector 62 generates and/or asserts the pace spike detect signal when any of the overrange conditions are met or the amplitude, slew rate, and pulse width analysis indicates that the presences of a pacing spike. The pace artifact analysis and the pace spike analysis may be capable of detecting pace artifacts and pace spikes that are not large enough to trigger the over-range conditions described above. Pace pulse detector 62 outputs the pace artifact detect signal to blanking control module 64 and outputs the pace spike detect signal to control module 30.

Blanking control module 64 initiates removal of the pulse from the electrical signal when the pace artifact detect signal is asserted. Although described herein as removing the pulse from the electrical signal, the pulse may not be completely removed from the electrical signal, but its effect on sensing accuracy is essentially neutralized. For example, the electrical signal may be modified such that the pulse is not mistaken for an intrinsic cardiac event (e.g., a ventricular event). As such, blanking control module 64 initiates removal of the pulse when any one of the over-range conditions is met or the pace artifact detection analysis indicates the presence of a pacing pulse that is high enough in amplitude and/or pulse width to impact the sensitivity for tachyarrhythmia detection. The modifications to the sensing channel to remove the pulse may continue for a predetermined period of time, until the pace artifact detect signal is deasserted, or until the pace artifact signal has been deasserted for a certain period of time. In some instances, blanking control module 64 may be configured to delay the initiation of the pulse removal to account for any delay of the signal through decimator 58 or other components of the sensing channel. The delay may be programmable and may have a value between ≥1 and ≤60 milliseconds (ms), and more preferably ≥5 and ≤25 ms. This may reduce the overall duration of the sensing channel modifications implemented to remove the pulse. In some instances, blanking control module 64 may use information regarding blanking done for a previous pulse to determine the length of blanking, to build confidence if blanking for current detected pacing pulse is appropriate, or the like.

In one example, blanking control module 64 may initiate blanking on only the sensing channel on which the pacing artifact was detected. In another example, blanking control module 64 may initiate blanking on all of the sensing channels when a pacing artifact is detected on any one of the sensing channels. For example, blanking control module 64 may cause a second blanking module in a second sensing channel to blank as well as blanking module 60 in the first sensing channel. When blanking is desired, blanking control module 64 provides a control signal to blanking module 60 to initiate blanking of the signal output from decimator 58. Blanking module 60 may, in one example, include a sample and hold circuit that holds the value of the signal at a current value in response to receiving the control signal from blanking control module 64. The current value may be a value of the electrical signal prior to the detected pulse. Blanking module 60 continues to hold the value of the sensed electrical signal until the blanking control module 64 removes or deasserts the control signal. In one example, blanking control module 64 may apply the control signal or hold signal, and thus cause blanking, for less than or equal to approximately forty (40) ms. In another example, blanking control module 64 may apply the hold signal for less than or equal to approximately thirty (30) ms. In another example, blanking control module 64 may apply the hold signal for less than or equal to approximately twenty (20) ms. In other embodiments, blanking module 60 may include an interpolation module that provides a linear interpolation or other interpolation between a first value at the time the control signal is initiated or asserted (e.g., prior to the detected pulse) and a second value at the time the control signal is removed or deasserted (e.g., subsequent the detected pulse). This period of time may be considered a blanking period as the electrical signal is essentially blanked to remove the pulse.

Blanking module 60 may, in some instances, also include a delay block that introduces a delay into the electrical signal prior to the sample and hold circuit to allow for detection of the pacing pulse by pace pulse detector 62 and analysis of the inputs by blanking control module 64 to determine whether to blank the electrical signal before the artifact from the pacing pulse has a chance to propagate into the sense and ECG outputs. The delay introduced into the sensing channel may be between approximately 1-20 ms depending up on where in the sensing channel the blanking occurs and whether or not blanking module 60 performs interpolation as described above. In some instances, this delay block may not exist or may be for a shorter period of time since the decimator 58 also provides some delay between the ADC output and the blanking module 60.

In other instances, pace pulse detector 62 may process and detect the pacing artifact faster than the time it takes the signal to propagate from ADC 56 to pulse removal module 60. In this case, pulse removal control module 64 may delay application of the signal that causes pulse removal module 60 to hold and/or interpolate the sensed signal to account for any delay of the sensed signal through decimator 58 and/or other component of the sensing channel. This may reduce the overall duration of the blanking time resulting in a more accurate sensed signal.

Figure 5A:
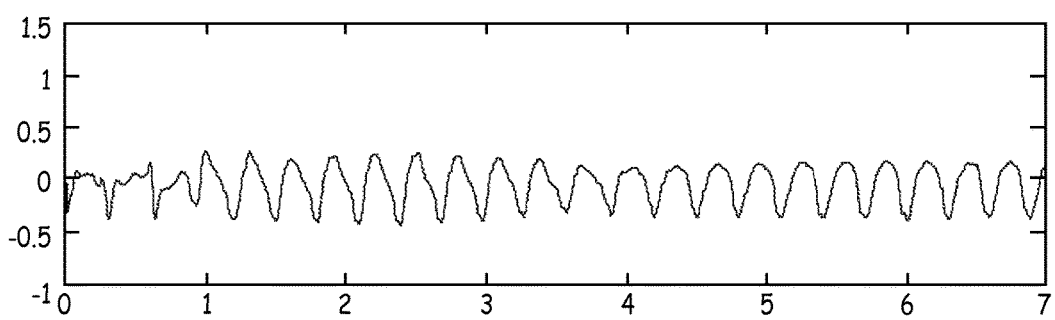
FIG. 5A illustrates a plot of the ECG of FIG. 4A after being modified to remove pacing pulses.
Figure 5B:
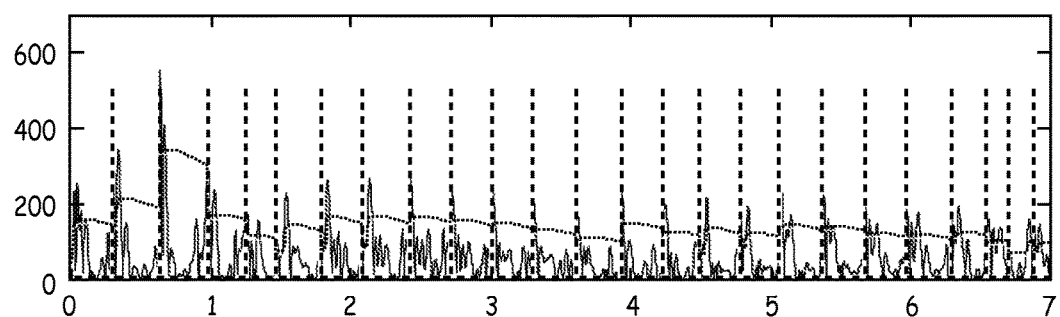
FIG. 5B illustrates a plot representing operations performed by sense digital filter on the ECG after modifying a sensed electrical signal to remove pacing pulses.

The output of blanking module 60 is provided to sense digital filter 66, ECG morphology filter 67, and diagnostic digital ECG filter 68, whose operation are described above. By providing the blanking described above, the pace artifact is significantly reduced as illustrated in the plots in FIG. 5A and FIG. 5B. FIG. 5A illustrates the same signal as FIG. 4A, but after the signal is modified to remove pacing pulses. The modification in the example of FIG. 5A includes a 24 ms blanking applied to each of the detected pace artifacts. Likewise, FIG. 5B illustrates the plot of operations within the digital sense filter 66. As can be seen in FIG. 5B, by blanking the sensing channel in response to detecting pace artifacts, the auto-adjusting threshold remains in a zone that is capable of detecting all of the cardiac events, thus reducing the likelihood of undersensing. Moreover, digital sense filter 66 does not falsely detect the pace spikes as intrinsic R-waves, thus reducing the likelihood of oversensing. The techniques of this disclosure therefore provide control module 30 with more accurate sensing information to monitor for tachyarrhythmia.

The sensing channel illustrated in FIG. 3 is one example sense channel. Other configurations of a sense channel or arrangement of components in the sense channel may be utilized without departing from the scope of this disclosure. In other embodiments, for example, pace pulse detector 62 may obtain its input from other components earlier in the sensing channel processing stage, e.g., from prefilter 50, preamplifier 52, or low-pass filter 54. In another example, blanking module 60 may be located elsewhere within the sensing channel, such as between preamplifier 52 and low-pass filter 54. In such an example, the blanking may be implemented using a resister in series with a switch to create a sample and hold circuit.

Figure 6:
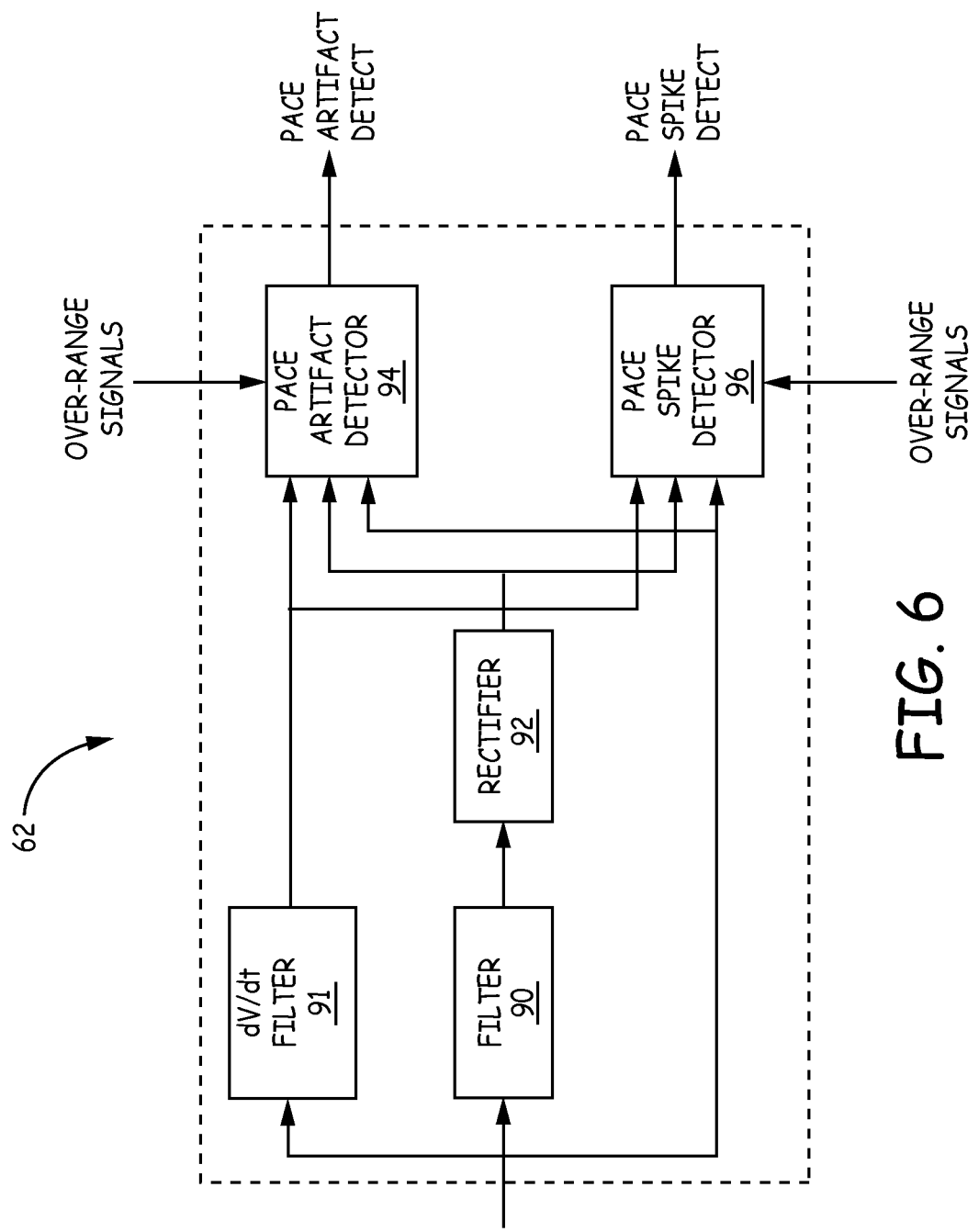
FIG. 6 is block diagram illustrating an example pulse detector.

FIG. 6 is block diagram illustrating an example pace pulse detector 62. Pace pulse detector 62 includes a filter 90, a derivative (dV/dt) filter 91, a rectifier 92, a pace artifact detector 94, and a pace spike detector 96. Pace pulse detector 62 inputs the signal output by ADC 56. This signal is provided to filter 91, dV/dt filter 91, pace artifact detector 94 and pace spike detector 96. However, the various components of pace pulse detector 62 may obtain the signal from other components of the sensing channel, such as directly from the preamplifier 52.

Filter 90 of pace pulse detector 62 filters the signal output from ADC 56. Filter 90 may be configured to pass electrical signals corresponding to pacing pulses and reject cardiac electrical signals. Filter 90 may, in one example, be a band-pass filter that passes signals having frequencies between approximately 100 Hz and 1000-4000 Hz. In another example, filter 90 may be a high-pass filter that passes signals having frequencies greater than 100 Hz. In other examples, filter 90 may be another type of filter, such as a derivative filter. In a further example, the signal may not be filtered at all. Rectifier 92 rectifies the filtered signal from filter 90. The rectified signal is then is provided to pace artifact detector 94 and pace spike detect detector 96.

The dV/dt filter 91 generates a difference signal (e.g., x(n)-x(n−1) of the output of ADC 56. The difference signal includes spikes that correspond with portions of the signal having high slew rates. The difference signal is also provided to pace artifact detector 94 and pace spike detect detector 96.

Pace artifact detector 94 and pace spike detector 96 analyze some or all of the raw input signal from ADC 56, the rectified signal from rectifier 92, the difference signal from dV/dt filter 91 to detect the presence of a pace artifact and a pace spike, respectively. In one example, pace artifact detector 94 and pace spike detect detector 96 may detect the pace artifact and pace spike, respectively, using only amplitude or only slew rate. In another example, pace artifact detector 94 and pace spike detect detector 96 may detect the pace the pace artifact and pace spike, respectively, using a combination of amplitude, slew rate, and pulse width. Depending on the type of analysis performed, pace pulse detector 62 may not include some of the components illustrated (e.g., filter 90, dv/dt filter 91, and/or rectifier 92). For example, if pace detector 94 and 96 do not analyze slew rate, detector 62 may not include dv/dt filter 91. However, in other embodiments, pace pulse detector 62 may include all the components and be configurable to analyze different aspects of the sensed signal.

Pace artifact detector 94 and pace spike detect detector 96 may compare raw input signal from ADC 56, the rectified signal from rectifier 92, the difference signal from dV/dt filter 91 to respective thresholds to detect the pace artifact and/or the pace spike. The thresholds of pace artifact detector 94 and pace spike detector 96 may be different such that the pace artifact detector 94 is configured to only detect pace artifacts having large enough amplitudes to impact the tachyarrhythmia detection algorithm performed by control module 30 while pace spike detector 94 is configured to detect pacing pulses regardless of whether they are large enough to impact the tachyarrhythmia detection algorithm performed by control module 30. Therefore, the pace artifact threshold(s) (e.g., artifact slew rate threshold or amplitude threshold) therefore are generally larger than the pace spike threshold(s) (e.g., spike slew rate threshold or amplitude threshold). As such, pace spike detector 94 will have a higher sensitivity than the pace artifact detector 96 so that it can detect pacing pulses with smaller amplitudes and pulse widths. In one example, the thresholds of pace pulse detector 62 may be set such that pace artifact detector 94 is configured to detect pacing pulses are greater than or equal to 2-10 mV at pulse widths of approximately 1 ms and pace spike detector 96 is configured to detect pacing pulses are greater than or equal to 1 mV at pulse widths of approximately 1 ms. However, the thresholds may be configurable and/or be configured to detect pacing pacing spikes and artifacts having different characteristics.

In some instances, some or all of the pace artifact thresholds and the pace spike thresholds may be automatically adjustable. For example, one or both of pace artifact amplitude threshold and the pace spike amplitude threshold may be dynamically adjusted based on the peak amplitude of the detected pulse to allow threshold to be raised higher to avoid EMI if the detected pace pulses are large in amplitude. Alternatively or additionally, one or both of the pace artifact amplitude threshold and the pace spike amplitude threshold may be dynamically adjusted based on a baseline R-wave amplitude. In this case, if the R-waves are large, the threshold for sensing pace artifacts and/or pace spikes may need to set higher. In one example, the increase may be proportionate, e.g., a 50% increase in sensed R-wave amplitude would lead to a 50% increase in pacing artifact detection threshold.

As further illustrated in FIG. 6, pace artifact detector 94 and pace spike detector 96 also receive the over-range signals from the various components of the sensing channel (e.g., the preamp over-range signal from preamplifier 52, the ADC input over-range signal from ADC 56, and the slew rate over-range signal from ADC 56). Based on the analysis of the over-range signals and the processing of the signals output by ADC 56, pace artifact detector 94 and pace spike detector 96 output a pace artifact detect signal and a pace spike detect signal, respectively. In one example, pace artifact detector 94 generates and/or asserts the pace artifact detect signal when any of the over-range conditions are met are met or the amplitude, slew rate, and/or pulse width analysis of the ADC output indicates the presence of a pacing artifact. Likewise, pace spike detector 96 generates and/or asserts the pace spike detect signal when any of the over-range conditions are met or the amplitude, slew rate, and/or pulse width analysis indicates the presences of a pacing spike.

The pace artifact detect signal is provided to blanking control module 64 to initiate blanking of one or more of the sensing channels, described in further detail below. Because blanking of the sensing channel(s) may introduce an artifact in the ECG signal, it is desired that blanking is only done when necessary to obtain good tachyarrhythmia detection sensitivity, thus the higher pace artifact thresholds.

The pace spike detect signal and, in some instances, the pace artifact detect signal, may be provided to control module 30 to be used as part of the tachyarrhythmia detection. The pace artifact detect signal and the pace spike detect signal may be provided directly to control module 30 by pace pulse detector 62 or relayed to control module via blanking control module 64. The pace artifact signal and the pace spike detect signal may be provided individually to control module 30. Alternatively, the pace artifact detect signal and the pace spike detect signal could be logically combined (e.g., logically OR'ed) and provided to control module 30. In instances in which multiple sensing channels are analyzed, the pace artifact signal and the pace spike detect signal for each of the sensing channels may be provided individually or logically combined.

The pace artifact detect signal and the pace spike detect signal may be provided to control module 30 using any of a number of techniques. For example, the pace artifact detect signal and the pace spike detect signal outputs from one or both of the sensing channels could be logically combined to generate a single output and used to generate an interrupt signal to control module 30. The advantage of combining signals and generating an interrupt is that it provides notification of the pacing event in a very short time allowing the control module 30 to quickly respond to a pacing pulse. The drawback is that it is possible that an excessive number of interrupts could be generated in certain conditions which may overload the ability of control module 30 to handle the interrupts or cause excessive current drain. Alternatively, the pace artifact detect signal and the pace spike detect signal from all active channels could be combined into a single register and continuously streamed over to control module 30 for storage in memory and later analysis. This provides the advantage of providing more information about the amplitude of the pacing pulse and which channel the pulse was detected on. It also allows control module 30 to process the pacing information on a regular schedule or when processing data for tachyarrhythmia detection rather than as an interrupt which reduce concerns with over-burdening control module 30 with interrupt handling. The drawback to this approach is that it requires additional memory and increases the latency from the pacing pulse being detected until control module 30 can act on the information. In some instances, additional information may be sent along with the pace pulse detection data. For example, the signal to control module 30 may also specify where the pace pulse detect occurs within the V-V interval. In some instances, ICD 20 or control module 30 may include an event queue that provides some or all of the information from sensing module 32 to control module 30. One example of such an event queue is described in U.S. Pat. No. 8,855,780 (Hansen et al.) entitled, "PACEMAKER EVENT QUEUE TO CONTROL DEVICE PROCESSOR OPERATING POWER," the contents of which is incorporated herein in their entirety.

Pace pulse detector 62 of FIG. 6 is one example of such a detector. In other embodiments, pace pulse detector 62 may include only a single detector instead of a pace artifact detector 94 and pace spike detector 96. In further embodiments, pace pulse detector 62 may include more than two pulse detectors. For example, pace pulse detector 62 may include a third pulse detector to detect noise or determine margin between a peak of the pacing signal and the respective threshold of pace artifact detector 94 or pace spike detector 96. This is described further with respect to FIG. 8. However, noise and/or signal margin may be detected using other techniques. For example, pace pulse detector 62 may include a peak detector configured to measure the peak of the detected pacing pulse and the peak may be used to determine whether pace artifact detector 94 and pace spike detector 96 have adequate margin for reliable detection of pacing pulses.

Figure 7:
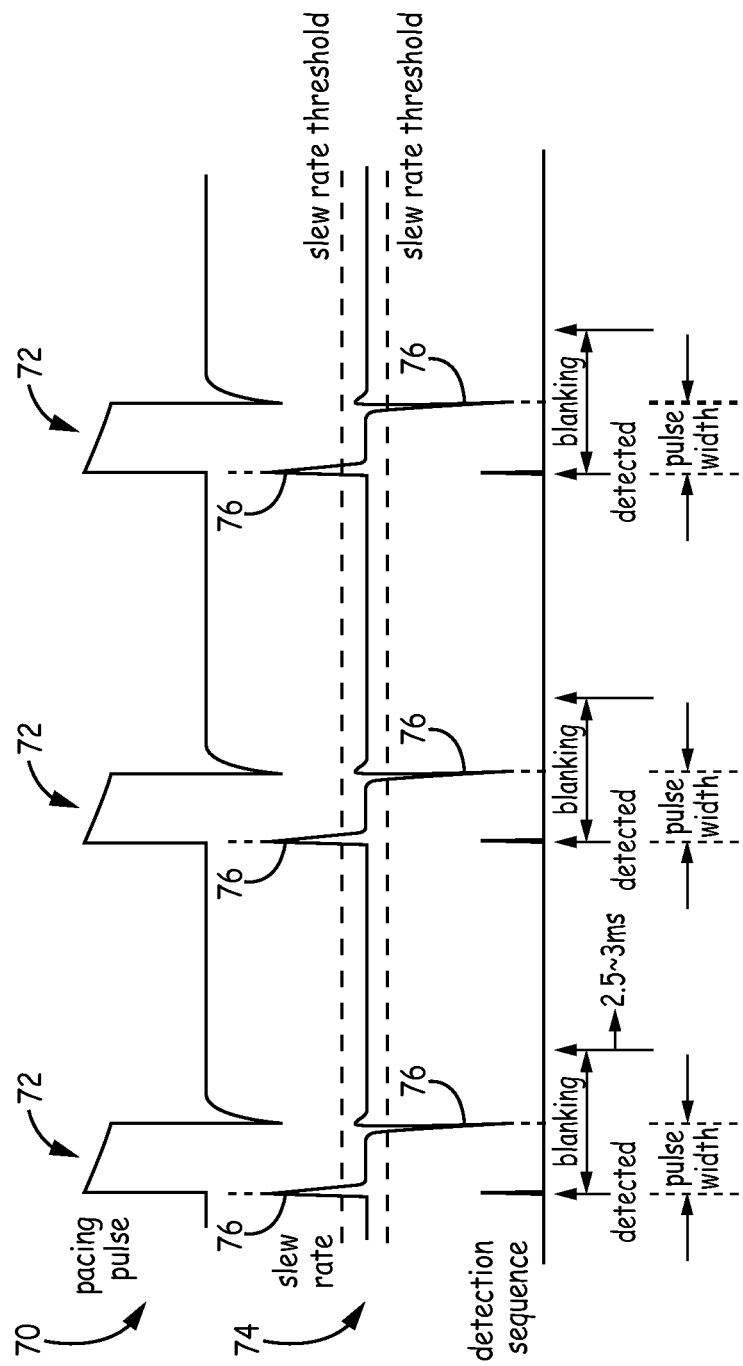
FIG. 7 is a conceptual diagram of a pace pulse detector analyzing the slew rate of the sensed electrical signals having pacing pulses.

FIG. 7 is a conceptual diagram illustrating example operation of pace pulse detector 62. FIG. 7 illustrates an example sensed electrical signal that includes a pacing train 70 that includes at least three pacing pulses 72. FIG. 7 also illustrates an example a slew rate signal 74, which may be output by filter 90 (e.g., a difference filter or first order derivative filter) of pace pulse detector 62. As illustrated in FIG. 7, slew rate signal 74 has spikes 76 that correspond with the edges of pacing pulses 72. Pace pulse detector 62 may compare slew rate signal 74 to a slew rate threshold 78 and when slew rate signal 74 exceeds the slew rate threshold, pace pulse detector 62 may detect the presence of a pacing spike. In order to avoid detecting the trailing edge of pacing pulse 72 as separate pace pulse, pace pulse detector 62 may not count any spike 76 that occurs within a particular period of time, e.g., 2 ms, from a previous spike 76 as a separate pacing pulse. In some instances, pace pulse detector 62 may, however, track these close proximity spikes to estimate pulse width of the pacing pulses. In other examples, detecting a slew rate that exceeds the slew rate threshold would result in further analysis of other characteristics of the detected signal, such as looking at the amplitude of the sensed electrical signal. In one instance, the example slew rate threshold may be equal to 4 mV/ms. However, other thresholds may be utilized.

Figure 8:
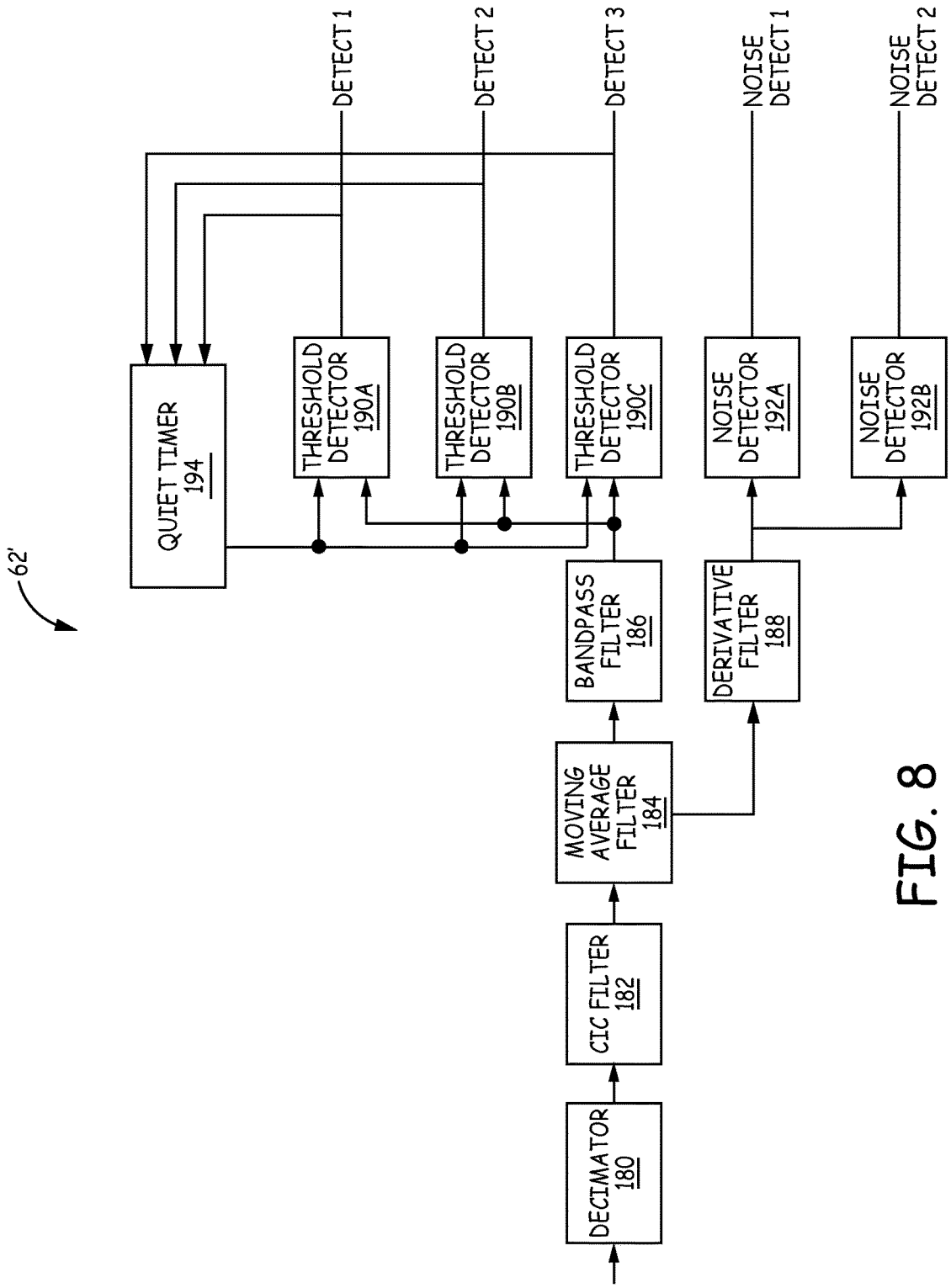
FIG. 8 is block diagram illustrating another example pulse detector.

FIG. 8 is a block diagram illustrating another example pace pulse detector 62'. Pace pulse detector 62' includes a decimator 180, CIC filter 182, moving average filter 184, bandpass filter 186, a derivative (dV/dt) filter 188, threshold detectors 190A-190C, and noise detectors 192A-192B. Pace pulse detector 62' may be utilized in a sensing channel, such as the sensing channel of FIG. 3. In other words, pace pulse detector 62' may be used in place of pace pulse detector 62.

Pace pulse detector 62' inputs the signal output by ADC 56. Pace pulse detector 62' makes use of decimation in order to attenuate high frequency noise and to allow the use of shorter filters at lower frequencies, thereby saving power. Decimator 180 decimates the digitized data output from ADC 56. In one example, decimator 180 may decimate the signal by a decimation factor of 2. For instance, ADC 56 may output an 8-bit signal at 32 kHz and decimator may reduce the sampling rate of the signal to output a 16 kHz signal. However, decimator 180 may perform decimation using other decimation factors.

Cascaded integrator-comb (CIC) filter 182 inputs the signal output by decimator 180. CIC filter 182 attenuates frequencies above a particular frequency band and further decimates the signal output by decimator 180. In one example, CIC filter 182 is a second-order CIC filter. In one example, CIC filter 182 may input a 16 kHz signal output by decimator 180 and decimate the signal to 4 kHz and increase resolution to 14 bits. CIC filter 182 may also attenuate frequencies above 4 kHz. In another example, the decimation function can be combined with the CIC filter to decimate directly from 32 Khz/8 bit down to 4 Khz/14 bit without using a separate decimate function. Other decimation and resolution changes may be used without departing from the scope of this disclosure.

Moving average filter 184 inputs the signal output by CIC filter 182. Moving average filter 184 averages a number of samples from the signal output by CIC filter 182 to produce each sample of the output signal. In this manner, moving average filter 184 may provide further high-frequency attenuation. In one example, moving average filter may be a second order moving average filter, but other moving average filters may be utilized.

Bandpass filter 186 inputs the signal output by moving average filter 184. Bandpass filter 186 passes frequencies within a certain range and rejects (or attenuates) frequencies outside of that range. In one example, bandpass filter 186 may be a 200 Hz bandpass filter. The output of bandpass filter 186 is provided concurrently to threshold detectors 190A-C.

Threshold detectors 190A-190C each compare the signal output from bandpass filter 186 to a respective amplitude threshold and output a signal (e.g., DETECT1, DETECT2, DETECT 3) based on the comparison. For example, when the signal output of bandpass filter 186 exceeds the respective amplitude threshold, the detect signal of the respective threshold detector 190 may go active for a period of time. The thresholds of each of threshold detectors 190 may be different from one another as explained in more detail below.

For instance, threshold detector 190A may have a first threshold, threshold detector 190B may have a second threshold that is smaller than the first threshold, and threshold detector 190C may have a third threshold that is smaller than both the first and second thresholds. The first threshold of threshold detector 190A may be set to a level to detect pace pulses having large enough amplitudes to be detected as intrinsic R-waves, VT, or VF by sense digital filter 66 and/or to impact the tachyarrhythmia detection algorithm performed by control module 30 (e.g., pace artifacts). In one example, the threshold of threshold detector 190A may be set such that threshold detector 190A detects pacing pulses having amplitudes that are greater than or equal to 2-10 mV for pulse widths of approximately 1 ms, similar to the pace artifact detector 94 of FIG. 6. In another example, the threshold of threshold detector 190A may be set such that threshold detector 190A detects pacing pulses having amplitudes that are greater than or equal to 4 mV for pulse widths of approximately 1 ms. However, the characteristics of the pacing pulses that the pace artifact detector is configured to detect may be different.

The threshold of threshold detector 190B may be set to a level at which threshold detector 190B detects pace pulses regardless of whether the pace pulse would be detected as an intrinsic R-wave and/or impact the tachyarrhythmia detection algorithm (e.g., pace spikes). As described above, the threshold of detector 190B is less than the threshold of detector 190A. In one example, the threshold of threshold detector 190B may be set such that threshold detector 190B detects pacing pulses having amplitudes that are greater than or equal to 1 mV and pulse widths of approximately 1 ms, similar to the pace spike detector 96 of FIG. 6.

The threshold of threshold detector 190C may be set to a level at which threshold detector 190C detects noise. As described in the example above, the threshold of detector 190C is less than the threshold of detector 190A and 190B. In this case, detector 190C detects signals which are lower in amplitude than would be detected by either 190A or 190B. As an example, threshold for detector 190C may be set a fraction or percentage of the threshold of detector 190B, e.g., 0.5X-0.75X where "X" is the threshold of detector 190B. These lower amplitude pulses may be interpreted as noise if they occur at higher frequencies or at different points in the cardiac cycle than expected for pacing pulses. Thus, threshold detector 190C can be set to detect EMI noise and artifacts, which might have different characteristics than pace artifacts/spikes, e.g., lower amplitude, different slew rate, and different frequency (e.g., rate at which pulses occur). In some instances, the threshold of detector 190C may be periodically adjusted to different levels to estimate the noise floor to enable thresholds 190A and 190B to be set to a level above the noise floor determined by using detector 190C.

In an alternative embodiment, threshold detector 190A may have a first threshold, threshold detector 190B may have a second threshold that is smaller than the first threshold, and threshold detector 190C may have a third threshold that is larger than either one or both the first and second thresholds. The first and second thresholds may be set at levels such that the first threshold detector 190A detects pace pulses (e.g., artifacts) having large enough amplitudes to be detected as intrinsic R-waves by sense digital filter 66 or to impact the tachyarrhythmia detection algorithm performed by control module 30 and the second threshold detector 190B detects pace pulses (e.g., spikes) regardless of whether the pace pulse would be detected as an intrinsic R-wave and/or impact the tachyarrhythmia detection algorithm. Example threshold values are described in the example above.

In this embodiment, however, the threshold of threshold detector 190C may be set to a level at which threshold detector 190C detects a larger signal amplitude than either threshold detector 190A or threshold detector 190B. In this manner, threshold detector 190C may be used to determine whether the thresholds of detectors 190A and/or 190B have sufficient margin. As described above, the threshold of detector 190C may be greater than either or both of the threshold of detector 190A and 190B. In one example, the threshold of detector 190C may be set to a level at which threshold detector 190C detects pulses that are a factor larger than detected by detector 190B, e.g., 1.5X-2X where "X" is the threshold of detector 190B. If it is determined that detector 190C is unable to detect pacing spikes detected by 190B, pace detector 62' may determine that detector 190B has inadequate margin. In an alternative embodiment, pace detector 62' may include peak detector instead of third threshold detector 190C that may be used to determine whether threshold detectors 190A and/or 190B have adequate margins. If adequate margin does not exist, one or more of the detect signals (DETECT1, DETECT2, DETECT3) may be ignored or disregarded. Alternatively, pace detector 62' may automatically adjust the threshold of detector 190B and/or 190A to a lower level in response to determining that there is inadequate margin.

In a further embodiment, detector 190C can be used both for verification of sufficient threshold to noise margin by using a threshold of, e.g., 0.5X-0.75X of threshold 190B, and for verification of signal to threshold margin by using a threshold of, e.g., 1.5X-2X of threshold 190B. This information can be used to adjust the threshold of 190B over time to provide both adequate threshold to noise ratio and signal to threshold ratio.

In some instances, pace detector 62' may include a plurality of quiet timers 194 that may inhibit their respective threshold detectors from indicating more than one pace detection per pace pulse. In one example, each threshold detector 190 may have a respective quiet timer 194. In another example, one or more of the threshold detectors 190 may have a common quiet timer 194. The outputs of quiet timers 194 goes active when the signal of a respective one of the threshold detectors 190 exceeds the programmed threshold. When one or more of the quiet timers 194 go active, the threshold detectors 190A-190C associated with those quiet timers do not detect a further pace pulse. In this manner, quiet timers 194 block further pace detects until the quiet timers 194 deactivates their outputs. In one example, quiet timers 194 may activate their outputs for ≥10 ms and ≤40 ms upon the threshold detector 190 associated with the quiet timer 194 outputs an active detect signal. In another example, quiet timers 194 may activate their outputs for 30 ms. In some instances, quiet timers 194 may operate in retrigger mode (a programmable feature), which restarts quiet timers 194 if another detection occurs while the output of quiet timer 194 is active. In other instances, pace pulse detector 62' does not include quiet timer 194.

In the example illustrated in FIG. 8, derivative filter 188 also obtains the signal output from moving average filter 184. Derivative filter 188 and noise detectors 192 process the sensed electrical signal in parallel with bandpass filter 186 and threshold detectors 190. Derivative filter 188 may be a first order difference derivative filter. For example, derivative filter may generate a difference signal (e.g., x(n)-x(n-1)) of the output of moving average filter 184. In other embodiments other derivative filters may be utilized.

In some embodiments, pace pulse detector 62' includes noise detectors 192 analyze the output of derivative filter 188 to detect noise signals. In other instances, no noise detection is performed by pace pulse detector 62'. In instances in which pace pulse detector 62' does include noise detectors 192, each of noise detectors 192 may monitor for a noise of a particular frequency, e.g., noise detector 192A may monitor for 60 Hz noise and noise detector 192B may monitor for 50 Hz noise. Pace pulse detector 62' may, in other embodiments, include only a single noise detector or more than two noise detectors.

In the example described above in which the output of the moving average filter is at 4 kHz, each of noise detectors 192 may include a zero-crossing counter that counts the number of 4 kHz cycles between zero crossings. Alternatively, there may be only a single zero-crossing counter that is shared by the noise detectors 192 and that tracks the number of 4 kHz cycles between zero crossings. Each of noise detectors 192 also includes a noise counter that is incremented and decremented as a function of the value of the zero-crossing counter when a zero-crossing occurs. Noise detectors 192 detect noise based on the value of the noise counter. In the case of noise detector 192A monitoring for 60 Hz noise, upon occurrence of a zero crossing, noise detector 192A determines the value of the zero-crossing counter and increments the 60 Hz noise counter if the value of the zero-crossing counter is within a range indicative of 60 Hz noise, e.g., is between 32 and 36, and decrements the 60 Hz noise counter if the value of the zero-crossing counter is not within the range indicative of 60 Hz noise, e.g., less than 32 or greater than 36. For 60 Hz noise, which has a period of 16.67 ms, it would be expected that a zero crossing occurs approximately every 8.33 ms. A 4 kHz clock cycle is 0.25 ms, so 8.33 ms is equal to a count of 33.3 clock cycles between zero crossings. The range is builds in some variance. Likewise, in the case of noise detector 192B monitoring for 50 Hz noise, upon occurrence of a zero crossing, noise detector 192B determines the value of the zero-crossing counter and increments the 50 Hz noise counter if the value of the zero-crossing counter is within a range indicative of 50 Hz noise, e.g., between 39 and 43 and decrements the 50 Hz noise counter if the value of the zero-crossing counter is not within the range indicative of 50 Hz noise, e.g., less than 39 or greater than 43. The range is selected in a manner similar to the 60 Hz noise range using the period of a 50 Hz signal in place of the 60 Hz noise signal. If either of the 60 Hz noise counter or the 50 Hz noise counter is greater than or equal to threshold, e.g., 7 in one example, the respective noise detect signal (e.g., NOISE DETECT1 or NOISE DETECT2, respectively) goes active. The particular noise detect signal remains active until the respective noise counter falls below a second threshold value, e.g., 4 in one example, at which point the active noise detects signal goes to inactive. Having the second threshold value be lower than the first threshold value provides a buffer so that the noise detector does not toggle between detecting noise and not detecting noise as frequently. Control module 30 may utilize the outputs of noise detectors 192A and/or 192B to determine if a pace detection is a false detection due to noise.

In other instances, the zero-crossing counter may count the number of data samples between each zero crossing and the thresholds could be set accordingly. In another alternative, timestamps of the zero crossings could be utilized to determine the frequency of the signals. In yet another instances, the noise detector may detect other noise or artifacts besides 50 and 60 Hz noise.

Figure 9:
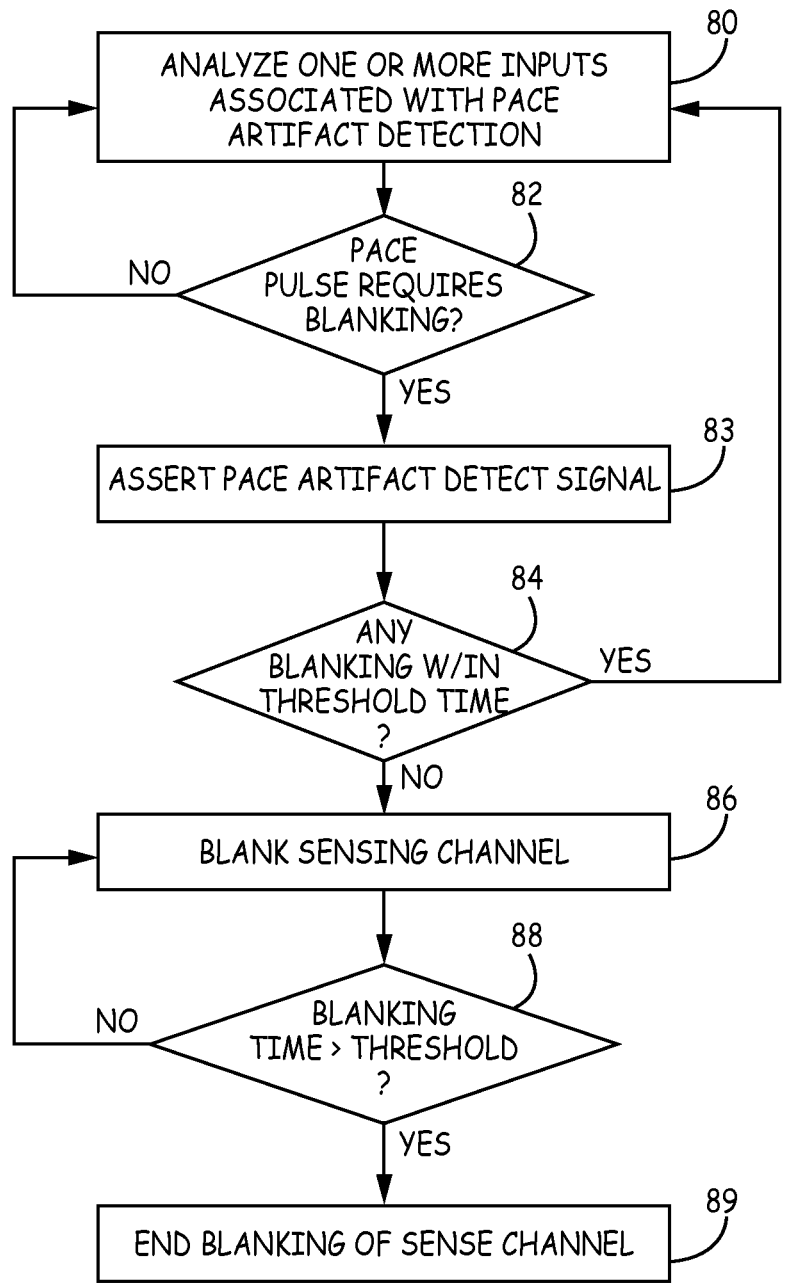
FIG. 9 is a flow diagram illustrating example operation of a sensing channel controlling the modification of the sensed electrical signal to remove pacing pulses from signals on one or more sensing channels based on input indicative of a pacing pulse.

FIG. 9 is a flow diagram illustrating example operation of blanking of one or more sensing channels in accordance with the techniques described herein. Initially, pace pulse detector 62 obtains and analyzes one or more inputs associated with detection of a pacing pulse in the sensing channel (80). In the example sensing module 30 of FIG. 3, for example, pace pulse detector 62 analyzes some or all of a pace artifact detect signal (e.g., based on slew rate, amplitude, pulse width or other characteristic of the received signal), preamp over-range signal, ADC input over-range signal, and ADC slew rate over-range signal. However, in other embodiments, only one of these signals or any combination of two or more of these signals may be analyzed by pace pulse detector 62. Additionally, other signals indicative of a pacing pulse or other artifact in the sensing channel may be analyzed by pace pulse detector 62. Different approaches using a single input or multiple inputs will result in different tradeoffs between sensitivity, specificity, complexity. In some instances, pace pulse detector 62 attempts to limit the blanking of the sensing channel to situations in which the pace pulse is likely to affect tachyarrhythmia detection sensitivity or specificity, e.g., higher amplitude pace pulses or pace artifacts.

Pace pulse detector 62 determines whether any of the inputs are indicative of a pacing pulse requiring blanking, i.e., a pacing artifact (82). As described above with respect to FIG. 3, a pace pulse may have an amplitude, slew rate, or other characteristic that is different than sensed signals (e.g., sensed R-waves or P-waves). For example, pace pulses having amplitudes of greater than approximately 10-20 mV may result in preamplifier 52 and/or ADC 56 to operate in one or more of the input over-range conditions. As another example, pace pulses may have slew rates that exceed the slew rate limit of ADC 56, thus causing activation of the ADC slew rate over-range signal. Likewise, the pace artifact detector 94 may detect a pace pulse likely to cause an artifact based on the amplitude, slew rate, or other characteristic of the signal from ADC 56 or other component. When none of the input signals is indicative of a pacing pulse requiring blanking ("NO" branch of block 82), blanking control module 64 continues to analyze the one or more inputs (80).

When any one of the input signals is indicative of a pacing pulse requiring blanking ("YES" branch of block 82), pace pulse detector 62 asserts the pace artifact detect signal (83). In response to the assertion of the pace artifact detect signal, Blanking control module 64 determines whether the sensing channel has been blanked within a threshold period of time (84). In one example, blanking control 64 will not blank the sensing channel until a period of at least 30-60 ms has passed since the last time the sensing channel was previously blanked. This is intended to prevent excessive blanking in a continuous EMI environment, but still allow blanking on both atrial and ventricular paced events at intervals less than approximately 200 ms. When blanking has been triggered within the threshold period of time ("YES" branch of block 84), blanking control module 64 will not blank the sensing channel and will continue to analyze the one or more inputs (80).

When blanking has not been triggered within the threshold period of time ("NO" branch of block 84), blanking control module 64 initiates blanking of the sensing channel (86). In one example, blanking control module 64 may initiate the blanking of the sensing channel by providing a control signal to blanking module 60 to cause the blanking module to hold the value of the sensed signal, as described above with respect to FIG. 3. In one example, blanking control module 64 may initiate blanking on only the sensing channel on which the pacing artifact was detected. In another example, blanking control module 64 may initiate blanking on all of the sensing channels when a pacing artifact is detected on any one of the sensing channels.

After initiating the blanking of the sense channel, blanking control module 64 determines whether the amount of time that the channel has been blanked is greater than a blanking threshold (88). In some instances, blanking control module 64 may be configured to blank for a predetermined period of time, e.g., 20 ms. When the sensing channel has not been blanked for the predetermined amount of time, ("NO" branch of block 88), blanking control module 64 continues to blank the sensing channel. When the sensing channel has been blanked for the predetermined amount of time, ("YES" branch of block 88), blanking control module 64 discontinues the blanking of the sensing channel (89).

In another embodiment, blanking control module 64 may not blank the sensing channel for a predetermined period of time. Instead, blanking control module 64 may continue to blank the sensing channel until all of the inputs no longer indicate presence of a pacing pulse requiring blanking, all of the inputs no longer indicate presence of a pacing pulse for a threshold period of time, e.g., 5-20 ms, allowing for sensing channel components to settle, or the amount of time since initiating the blanking of the sensing channel is greater than or equal to a maximum blanking duration, e.g., approximately 10-30 ms.

Figure 10:
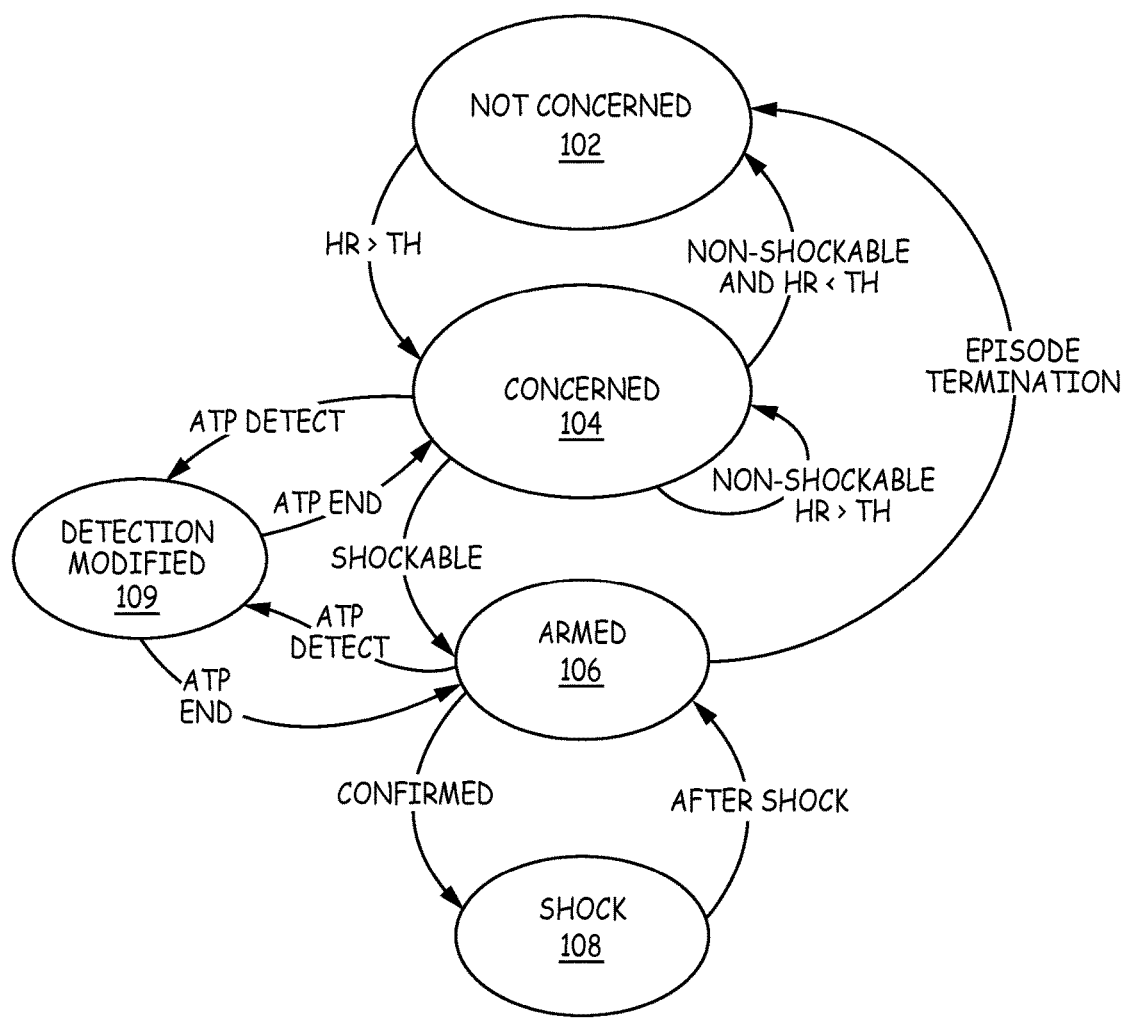
FIG. 10 is a state diagram of an example tachyarrhythmia detection algorithm.

FIG. 10 is a state diagram 100 of an example tachyarrhythmia detection algorithm. During normal operation, ICD 20 operates in a not concerned state 102 in which control module 30 estimates the heart rate of the sensed electrical signals on one or more sensing channels. Control module 30 of ICD 20 may measure a plurality of R-R intervals (i.e., intervals between consecutive sensed ventricular events) on the sensing channel and estimate the heart rate of the sensing channel based on the plurality of measured R-R intervals. In one example, control module 30 stores the most recent 12 R-R intervals on the sensing channel. However, control module 30 may store more or fewer than the 12 most recent R-R intervals. To estimate the heart rate, control module 30 may sort the stored R-R intervals from shortest to longest R-R intervals and estimate the heart rate using only a subset of the R-R intervals. In one example, control module 30 may estimate the heart rate as an average of a subset of the measured R-R intervals (e.g., the average of the 7th through 10th shortest R-R intervals of the most recent 12 R-R intervals). More or fewer R-R intervals may be used in the estimation of the heart rate. As another example, control module 30 may estimate the heart rate using the median of the measured R-R intervals or other specific R-R interval in the group, e.g., the $9^{th}$ shortest R-R interval. The example heart rate estimation techniques described above provide an estimate of the heart rate that is less susceptible to oversensing while maintaining reasonable sensitivity to short R-R intervals as in the case of VT or VF.

In the example described herein, ICD 20 independently estimates the heart rate on two of the sensing vectors described above with respect to FIG. 1 and compares the estimated heart rates to a tachyarrhythmia heart rate threshold, e.g., a VT/VF threshold. In one example, the tachyarrhythmia heart rate threshold may be set to 180 beats per minute. However, other thresholds may be used. Moreover, in other instances, control module 30 may analyze only a single sensing vector or more than two sensing vectors in other instances. Example operation in a "not concerned" state is described in paragraphs [0064]-[0075] of the specification as filed and FIG. 7A and FIG. 8 of U.S. Pat. No. 7,761,150 to Ghanem et al., entitled "METHOD AND APPARATUS FOR DETECTING ARRHYTHMIAS IN A MEDICAL DEVICE" (referred to herein as Ghanem et al.) The entire content of the referenced portions of Ghanem et al. are incorporated by reference herein in their entirety.

When control module 30 determines that the heart rate on one or both of the sensing vectors is above the tachyarrhythmia heart rate threshold, control module 30 transitions to a concerned state 104. In the concerned state 104, control module 30 discriminates rhythms requiring shock therapy from those that do not require shock therapy using a combination of heart rate and ECG signal morphology information. In the concerned state 104, for example, control module 30 analyzes the morphology metrics of a plurality of predetermined segments of the sensed electrical signals and classifies each segment as shockable or non-shockable. Control module 30 may perform this morphology analysis on the electrical signals in both sensing vectors in parallel.

In one example, control module 30 analyzes the morphology over a plurality of 3-second segments of the electrical signals and, for each of the 3-second segments, classifies the EGM in that particular 3-second segment as shockable or non-shockable. In other examples, the length of the segment analyzed by control module 30 in the concerned state may be shorter or longer than 3 seconds.

The morphology analysis in this concerned state may include a gross morphology analysis in which metrics are computed for the electrical signal over the entire segment, without regard for the location of QRS complexes. The morphology metrics may include, in one example, the signal energy level, noise to signal ratio, muscle noise pulse count, normalized mean rectified amplitude, the mean frequency, the spectral width, and the low slope content. These metrics are exemplary of the type of metrics that may be used and should not be considered limiting of the techniques described herein. Other gross morphology metrics may be used in addition to or instead of the metric listed above.

Control module 30 analyzes the gross morphology metrics to classify the segment as shockable or non-shockable. Control module 30 may analyze one or more of the gross morphology metrics of the segment to determine whether the signal in that particular segment is corrupted by noise and/or artifact. If so, control module 30 may classify the segment as non-shockable or classify the segment based on the classification of the same segment in the other sensing vector. If the control module determines that the signal in the segment is not corrupted by noise and/or artifact, control module 30 analyzes one or more of the gross morphology metrics to determine whether the signal in the segment is in either a VT or a VF shock zone and, if so, classifies the segment as shockable. If the segment is determined to not be in the VT or VF shock zone, the segment is classified as non-shockable. Example analysis of gross morphology during operation in a "concerned" state is described in paragraphs [0076]-[0130] and [0138]-[0141] of the specification as filed and FIGS. 7B-7E, 7H, 7I, FIGS. 9A-9C, FIG. 10, and FIGS. 11A-B of Ghanem et al. The entire content of the referenced portions of Ghanem et al. are incorporated by reference herein in their entirety.

If the gross morphology classification of the segment is shockable, control module 30 may, in some instances, also analyze a morphology of the QRS complexes or beats within the segment to classify the segment as shockable or non-shockable. This analysis may be referred to as beat-based morphology analysis since the control module 30 is only analyzing the morphology of windows around a beat instead of the entire segment. The window may, for example, have a range between 120-200 ms. In one example, control module 30 may compare the morphology of the beat within the window to a predetermined template morphology to determine if the beat matches the predetermined template (e.g., has a matching score threshold that is greater than or equal to 60%). If more than the threshold number of beats within the segment, e.g, more than 75% of the beats within the segment, do not match the template the segment is classified as shockable. Otherwise the segment is classified as non-shockable. As such, when gross morphology and beat-based morphology are both analyzed, the segment must satisfy both analyses to be classified as shockable. In other embodiments, however, control module 30 may make the classification of the segments as shockable or non-shockable based only on the gross morphology analysis described above. One example beat-based morphology analysis of segments of the sensed electrical signal is described in U.S. patent application Ser. No. 14/250,040, entitled "METHOD AND APPARATUS FOR DISCRIMINATING TACHYCARDIA EVENTS IN A MEDICAL DEVICE USING TWO SENSING VECTORS," particularly in FIGS. 4, 10, and 11 and the associated description of those figures. The entire content of that application is referenced herein in its entirety.

Control module 30 stores the classification of the segments of both the sensing vectors and analyzes the classifications of the plurality of segments to determine whether or not to transition to an armed state in which capacitor charging begins. If control module 30 determines that the rhythm does not require shock therapy (e.g., less than a threshold number of segments are classified as shockable) and the heart rate on at least one sensing vector is less than or equal to the threshold heart rate, control module 30 transitions to the not concerned state 102. If control module 30 determines that rhythm does not require shock therapy, but the heart rate in both sensing vectors is greater than the threshold heart rate, control module 30 continues analyzing the morphology metrics over subsequent 3-second segments of the electrical signals in the concerned state 104. If control module 30 determines that the rhythm is shockable during the concerned state 104 (e.g., greater than 2 of 3 segments classified as shockable in both sensing channels), control module 30 transitions to an armed state 106.

In the armed state 106, control module 30 initiates charging of the defibrillation capacitors. Additionally, control module 30 continues to analyze signal morphology (gross morphology alone or gross and beat-based morphology) for termination of the shockable rhythm. Control module 30 may, for example, continue to classify segments of the sensed signal as shockable or non-shockable as described above with respect to the concerned state 104 and analyze the number of segments classified during either the concerned state 104 or the armed state 106 as shockable. If control module 30 determines that the rhythm requiring shock therapy has terminated, control module 30 returns to the not concerned state 102. Control module 30 may determine that the rhythm has terminated, for example, when less than 3 of the last 8 segments are classified as shockable in both sensed signals and the heart rate in at least one of the sensed signals is less that the tachyarrhythmia heart rate threshold. If control module 30 determines the rhythm requiring shock therapy is still present once the charging of the capacitors is completed, e.g., at least five out of the last eight three-second segments are classified as being shockable, control module 30 transitions from the armed state 106 to a shock state 108. Example operation in an "armed" state is described in paragraphs [0131]-[0136] of the specification as filed and FIG. 7F of Ghanem et al. The entire content of the referenced portions of Ghanem et al. are incorporated by reference herein in their entirety.

In the shock state 108, control module 30 controls therapy module 34 to deliver a shock via a therapy vector that includes defibrillation electrode 24 and returns to the armed state 106 to evaluate the success of the therapy delivered. For example, control module 30 may determine whether the tachyarrhythmia has terminated and transition to the non-concerned state or determine whether the tachyarrhythmia is redetected. The control module 30 may, for instance, redetect the tachyarrythmia when at least 2 of 3 segments classified as shockable in both sensing channels. Example operation in a "shock" state is described in paragraph [0137] of the specification as filed and FIG. 7G of Ghanem et al. The entire content of the referenced portions of Ghanem et al. are incorporated by reference herein in their entirety.

One example technique for operating in the non-concerned state, the concerned state, the armed state and the shock state is described in Ghanem et al., which is incorporated by reference herein in its entirety.

When operating in a detection state in which the morphology metrics of predetermined segments of the sensed electrical signal are being analyzed, e.g., in the concerned state 104 or the armed state 106 of FIG. 9, control module 30 may detect a pacing train and, in response to detecting the pacing train transition, transition to a modified detection state 109 in which one or more tachyarrhythmia detection modifications are made. As described above, delivery of pacing by pacing device 16 may interfere with tachyarrhythmia detection by control module 30. Therefore, control module 30 responds to delivery of pacing by modifying the tachyarrhythmia detection analysis to reduce the likelihood of corruption. As will be described further with respect to flow diagrams below, tachyarrhythmia detection will be modified during the pacing provided by pacing device 16.

Figure 11:
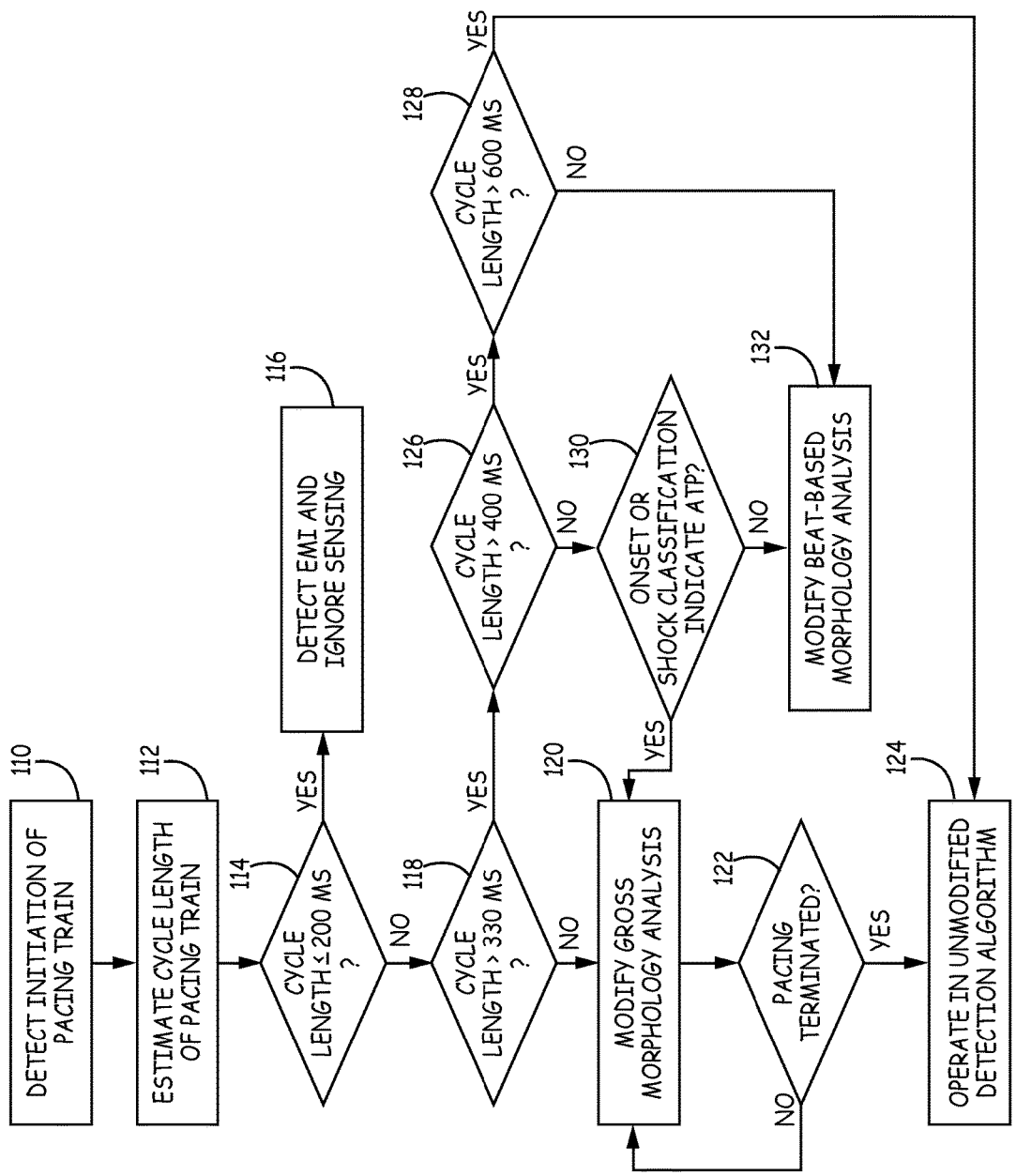
FIG. 11 is a flow diagram illustrating example operation of a control module detecting a pacing train and modifying tachyarrhythmia detection in response to detecting the pacing train.

FIG. 11 is a flow diagram illustrating example operation of control module 30 detecting a pacing train and modifying tachyarrhythmia detection in response to detecting the pacing train. Initially, control module 30 analyzes the pace spike detect signal (or the logical combination of the pace spike detect signal and the pace artifact detect signal) from one or more sensing channels to detect initiation of a pacing train (110). In one example, control module 30 detects the initiation of the pacing train when pace spike detect signal identifies two pacing spikes within 1500 milliseconds of one another. In other words, the start of a pacing train is detected upon the detection of a single paced cycle of less than 1500 ms. However, control module 30 may use a different threshold than 1500 ms to detect the initiation of the pacing train.

Control module 30 estimates a cycle length of the pacing train (112). In one example, control module 30 may compute the two most recent cycle lengths of the pacing train using the three most recently detected pacing spikes and estimate the cycle length of the pacing train as the shortest of the two most recent cycle lengths. This allows for some underdetection of pacing spikes within the pacing train. For example, if 3 out of the last 4 paces are detected, the observed cycle lengths might be X and 2X, control module 30 would estimate the cycle length of the pacing train to be X. In other instances, control module 30 may use more than two most recent cycle lengths (e.g., by using the 3, 4, 5, or more most recent cycle lengths) or only a single cycle length. Moreover, control module 30 may estimate the cycle length of the pacing train using other techniques, such as an average or median of the plurality of most recent cycle lengths instead of selecting the shortest of the two most recent cycle lengths as the estimated cycle length of the pacing train.

Control module 30 determines whether the estimated cycle length is less than or equal to a first cycle length threshold (114). The first cycle threshold may be minimum cycle length that may be confidently classified as ATP. In one example, the minimum cycle length threshold may be equal to 200 milliseconds. When the estimated cycle length is less than or equal to the first cycle length threshold ("YES" branch of block 114), control module 30 determines that the detected pacing train is likely EMI and the signal is ignored (116).

Figure 12:
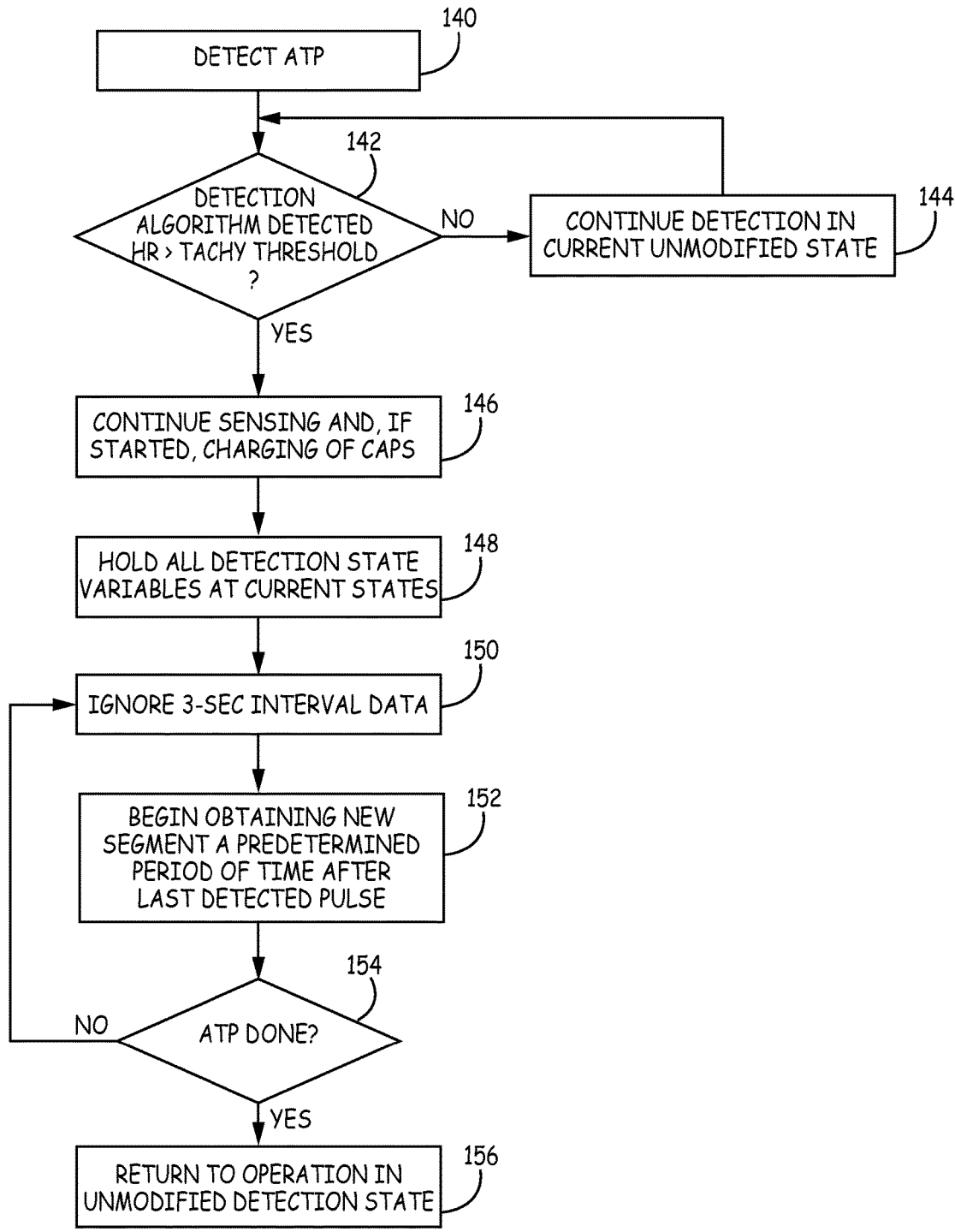
FIG. 12 is a flow diagram illustrating example operation of a control module implementing a modified tachyarrhythmia detection algorithm to account for ATP.

When the estimated cycle length is greater than the minimum cycle length threshold ("YES" branch of block 114), control module 30 compares the estimated cycle length to a second cycle length threshold (118). The second cycle length threshold may be a maximum cycle length that can be confidently classified as ATP. In one example, the second cycle length threshold may be equal to 330 milliseconds. When the estimated cycle length is less than or equal to the second cycle length threshold ("NO" branch of block 118), control module 30 determines the pacing train is ATP and modifies the detection algorithm to account for the presence of ATP (120). FIG. 12 below describes one example of detection modifications made to account for ATP in the sensed electrical signal. In that example, the tachyarrhythmia detection is partially inhibited until ATP has terminated. Other modifications, however, may be made to account for the ATP in the sensed signals. In other examples, additional analysis other than looking at the estimated cycle length may be performed to more confidently conclude that the detected pacing train with the estimated cycle length is ATP. For example, control module 30 may analyze a regularity of the pacing pulse intervals, consistency of the pacing artifact amplitude, consistency of the pacing pulse slew rate, and/or consistency of the pacing pulse polarity. Typically, ATP would be consistent in some, if not all, of these aspects.

Control module 30 continues to analyze the pace spike detect signal and/or the pace artifact detect signal from sensing module 32 to determine whether the pacing train has terminated (122). For instance, control module 30 may detect that the pacing train has terminated when one of two conditions are met: (1) a pacing spike has not been detected for a threshold period of time or (2) the amount of time since detecting the initiation of the pacing train exceeds a threshold amount of time. In one example, control module 30 may detect the end of the pacing train when no pace pulse has been detected on the pace spike detect signal and/or the pace artifact detect signal for at least a multiple of the estimated cycle length of the pacing spikes. The multiple may be any number greater than 2. In one particular example, the multiple may be 2.25 times the estimated cycle length. In other instances, however, control module 30 may utilize a different multiple. Alternatively, control module 30 may detect the end of the pacing train after a particular amount of time has elapsed from initiation of the pacing train. For example, control module 30 may detect the end of the pacing train 3 seconds, 4, seconds, 5 seconds, or other predetermined period of time after initiation of the pacing train. Such a feature sets a maximum duration allowed for detecting ATP.

When control module 30 determines that the pacing train has not terminated ("NO" branch of block 122), control module 30 continues to modify the detection algorithm to account for the presence of ATP (120). When control module 30 determines that the pacing train has terminated ("YES" branch of block 122), control module 30 reverts to the unmodified tachyarrhythmia detection algorithm (124).

Referring back to decision block 118, when the estimated cycle length is greater than the second cycle length threshold ("YES" branch of block 118), control module 30 determines whether the cycle length is greater than a third cycle length threshold (126). In one example, the third cycle length may be equal to 400 ms. When the estimated cycle length is greater than 330 ms and less than 400 ms ("NO" branch of block 126), the pacing train cannot be confidently classified as ATP or fast bradycardia pacing based on the estimated cycle length alone. Control module 30 thus determines whether there is onset leading up to the pacing or shockable rhythm classification leading up to the pacing (130). If the pacing is ATP, it will be preceded by a sudden increase in HR (an "onset"), and likely will have a shockable rhythm classification for segments prior to the pacing. In contrast, if the pacing is fast bradycardia pacing, it will have a slow rise in heart rate over time (i.e., no onset), and likely will have a non-shockable classification for those segments prior to pacing. In other examples, additional analysis other than looking at onset or rhythm classifications leading up to the pacing may be performed to more confidently conclude that the detected pacing train with the estimated cycle length is ATP. For example, control module 30 may analyze a regularity of the pacing pulse intervals, consistency of the pacing artifact amplitude, consistency of the pacing pulse slew rate, and/or consistency of the pacing pulse polarity. Typically, ATP would be consistent in some, if not all, of these aspects.

When control module 30 determines that there is onset leading up to the pacing or shockable rhythm classifications leading up to the pacing ("YES" branch of block 130), control module 30 determines the pacing train is ATP and modifies the detection algorithm to account for the presence of ATP (120). When control module 30 determines that there is no onset leading up to the pacing or non-shockable rhythm classifications leading up to the pacing ("NO" branch of block 130), control module 30 detects fast bradycardia pacing and modifies the detection algorithm to account for the fast bradycardia pacing (132). In one example, a new beat-based morphology consistency discriminator is added to the tachyarrhythmia detection algorithm. Other modifications, however, may be made to account for the fast bradycardia pacing in the sensed signals. Control module 30 continues to operate in the modified beat-based detection algorithm until the cycle length (e.g., heart rate) of the rhythm falls outside of the VT/VF zone.

Returning to decision block 126, when the estimated cycle length is greater than the third cycle length threshold ("YES" branch of block 126), control module 30 compares the estimated cycle length to a fourth cycle length threshold (128). The fourth cycle length threshold may correspond to a maximum fast bradycardia cycle length and may, in one example, be equal to 600 ms. When the estimated cycle length is greater than the fourth cycle length threshold ("YES" branch of block 128), control module operates in the unmodified detection algorithm. When the estimated cycle length is greater than the fourth cycle length threshold ("NO" branch of block 128), control module 30 detects fast bradycardia pacing and modifies the detection algorithm to account for the fast bradycardia pacing (132).

The thresholds used in the example described in FIG. 11 may be used to detect pacing spike trains of a single chamber pacemaker. The thresholds may be different for dual chamber or CRT pacemakers as there may be different timing between paces (e.g., AV delay or VV delay). Other analysis techniques may need to be performed for pacing trains provided to more than one chamber of the heart.

FIG. 12 is a flow diagram illustrating example operation of control module 30 implementing a modified tachyarrhythmia detection algorithm to account for ATP. Initially, control module 30 detects an ATP train (140). In one example, control module 30 may detect the ATP train when an estimate a cycle length of the detected pacing train is between 200-330 ms or between 330-400 ms with heart rate onset of shockable classifications immediately prior to the detection of ATP. However, in other examples, control module may detect ATP pacing using different cycle length ranges.

Control module 30 determines whether the tachyarrhythmia detection algorithm has detected a heart rate that exceeds the tachyarrhythmia detection threshold (142). As described above with respect to FIG. 10, control module 30 operates in non-concerned state 102 in which only the heart rate is analyzed on the selected sensing vectors until the heart rate exceeds the tachyarrhythmia detection threshold, e.g., 180 beats per minute. When the estimated heart rate on both of the sensing vectors does not exceed the tachyarrhythmia detection threshold ("NO" branch of block 142), control module 30 continues to operate in the unmodified non-concerned state 102 (144).

When the tachyarrhythmia detection algorithm detects or previously detected, e.g., prior to detecting the ATP train, that the heart rate exceeds the tachyarrhythmia detection threshold ("YES" branch of block 142), control module 30 is most likely operating in one of the concerned state 104 or the armed state 106 of FIG. 10. As described above with respect to FIG. 10, during the concerned state 104 and the armed state 106, control module 30 is classifying segments of the sensed electrical signal as shockable or non-shockable based on the analysis of the gross morphology of the segments and/or the beat-based morphology within the segments.

Control module 30 continues sensing on the sensing channels and, if operating in the armed state 106, continues charging the defibrillation capacitors (146). Control module 30 holds all detection state variables at current states (148). For example, the buffer maintaining the most recent, e.g., eight, classifications of the segments as shockable and non-shockable will be maintained. Control module 30 will ignore any incomplete segment of the EGM or retrospective segment of the EGM that includes the the ATP train (150).

Control module 30 begins a new segment (e.g., 3-second segment) a predetermined period of time after the last detected pace pulse (152). For example, control module 30 may begin a new 3-second segment 330 ms after the last detected pace pulse. In other instances, control module 30 may begin the new segment (e.g., 3-second segment) of the signal after the last detected pace pulse based on the estimated cycle length. Control module 30 determines whether the ATP train has terminated (154). As described above, for example, control module 30 may detect that the pacing train has terminated when one of two conditions are met: (1) a pacing pulse has not been detected for a threshold period of time (e.g., 2.25X the estimated cycle length or some predetermined threshold) or (2) the amount of time since detecting the initiation of the pacing train exceeds a threshold amount of time (e.g., 5 seconds). Note that the criteria for detecting the end of a pacing train will be met after initiation of obtaining the new 3-second morphology segment. In other words, the start of a possible 3 second morphology analysis window may be initiated before the end of a pacing train is detected.

When the end of the pacing train is not detected ("NO" branch of block 154), control module 30 ignores the segment of data and a new possible morphology segment will again be initiated a predetermined period of time after the most recently detected pacing pulse (150, 152). In another example, control module 30 may not obtain the morphology segment (e.g., 3-second segment) until after detecting the ATP has terminated in block 154. When control module 30 determines that the ATP train has terminated ("YES" branch of block 154), control module 30 returns to normal detection operation and performs the morphology analysis of the new morphology segment to determine whether the segment is shockable or non-shockable (156). Control module 30 will therefore update the detection state as if it were contiguous with the pre-ATP analysis.

Figure 13:
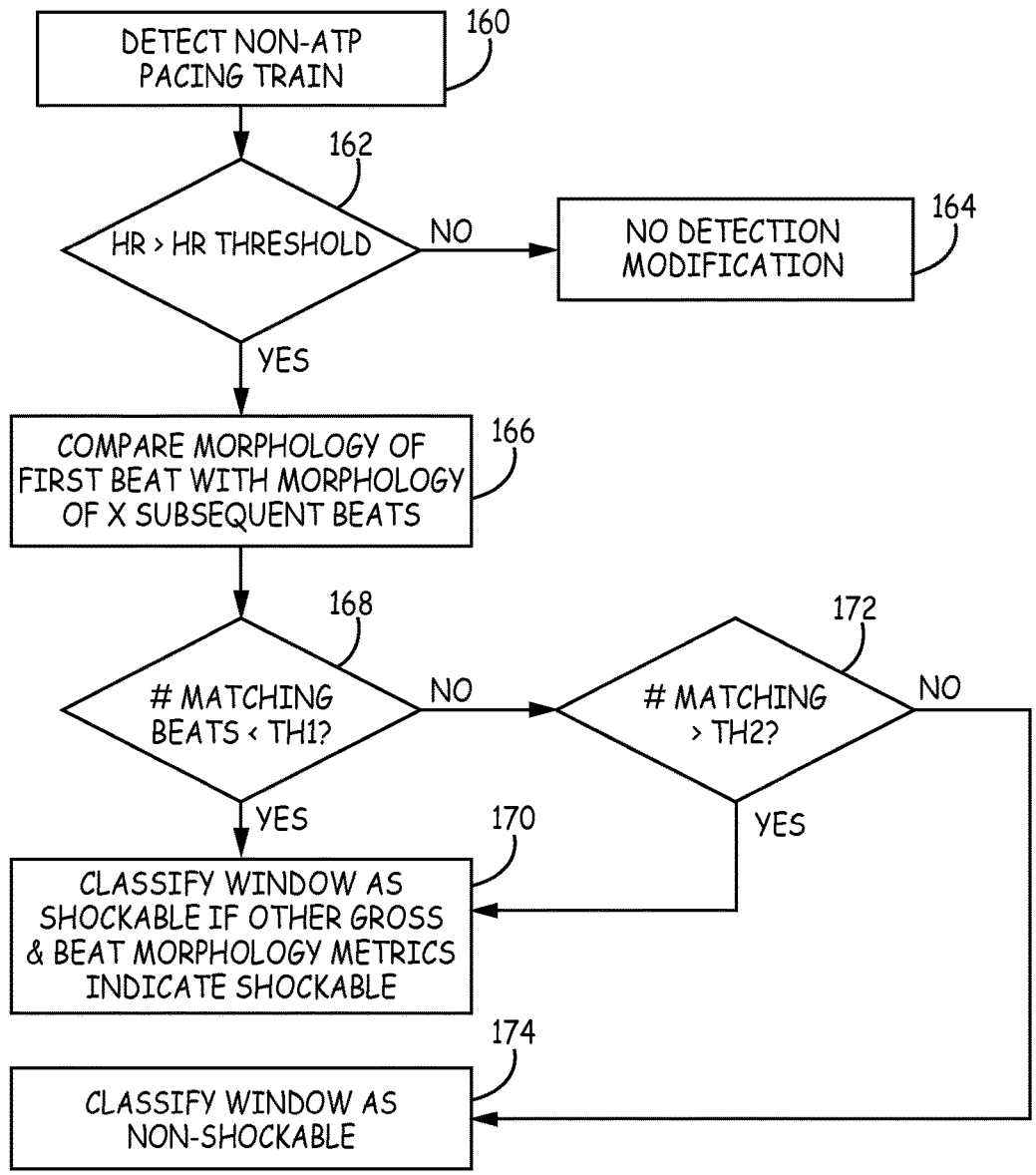
FIG. 13 is a flow diagram illustrating example operation of a control module modifying a tachyarrhythmia detection algorithm to account for fast bradycardia pacing.

FIG. 13 is a flow diagram illustrating example operation of control module 30 modifying a tachyarrhythmia detection algorithm to account for fast bradycardia pacing. Initially, control module 30 detects a fast bradycardia pacing train (160). In one example, control module 30 may estimate a cycle length of a detected pacing train and detect the fast bradycardia pacing train when the estimated cycle length of the detected pacing train is greater than 400 ms, as described above with respect to FIG. 11. However, in other examples, control module may detect fast bradycardia pacing using a different cycle length threshold or other technique.

Control module 30 determines whether the heart rate as sensed on both of the sensing vectors is above a tachyarrhythmia heart rate threshold, e.g., 180 beats per minute (162). When control module 30 determines that the heart rate is not above the tachyarrhythmia heart rate threshold ("NO" branch of block 162), control module 30 does not make any tachyarrhythmia detection modifications (164). When control module 30 determines that the heart rate is above the threshold heart rate ("YES" branch of block 162), control module 30 implements an additional beat-based morphology analysis to monitor the consistency of the morphology. One example scenario that may result in a shockable classification when no shock is necessary is when the paced evoked response results in double counting because of the wide QRS and large T-waves. The ECG morphology surrounding such a scenario would be an A-B-A-B pattern caused by the consistent oversensing and if the pacing pulses lead to consistent capture.

To identify this scenario, or other scenarios that may cause inappropriate shock classifications, control module 30 compares a morphology of a first sensed event within the current segment with a morphology of a predetermined number of subsequent sensed events within the segment and classify each of the comparisons as a match or non-match (166). Each sensed event or beat may be classified as matching when a matching score that is greater than or equal to a threshold, e.g., 60%, otherwise the beat is classified as non-matching. In other instances, control module 30 may compare a morphology of first sensed event after detection of ATP with the morphology of the subsequent sensed events within the segments and classify each of the comparisons as a match or non-match. Whereas the beat-based morphology analysis performed in the concerned state 104 and the armed state 106 described above in FIG. 10 compares the morphology of the beat window to a predetermined template of an intrinsic heart rate morphology, the additional beat-based morphology consistency discriminator compares the morphology of the first sensed event of the tachyarrhythmia with morphology of a predetermined number of subsequent sensed events. In one example, the predetermined number of subsequent sensed events is equal to 11. However, the predetermined number may be greater than or less than 11.

Control module 30 determines whether the number of subsequent sensed events having morphologies that match the morphology of the first sensed event of the segment is less than a first threshold (168). In one example, the first threshold may be equal to 3 when the predetermined number of subsequent sensed events is equal to 11. However, the first threshold may be equal to other values, particularly when the predetermined number of subsequent sensed events is greater than or less than 11. When control module 30 determines that the number of the subsequent sensed events having morphologies that match the morphology of the first sensed event of the segment is less than the first threshold ("YES" branch of block 168), control module 30 characterizes the segment as shockable if the other gross and beat-based morphology analyses indicate shockable (170). This may occur, for example, when the tachyarrhythmia is VF or polymorphic VT.

When control module 30 determines that the number of the subsequent sensed events having morphologies that match the morphology of the first sensed event of the segment is greater than or equal to the first threshold ("NO" branch of block 168), control module 30 determines whether the number of subsequent sensed events having morphologies that match the morphology of the first sensed event of the segment is greater than a second threshold (172). In one example, the second threshold may be equal to 7 when the predetermined number of subsequent sensed events is equal to 11. However, the second threshold may be equal to other values, particularly when the predetermined number of subsequent sensed events is greater than or less than 11.

When control module 30 determines that the number of the subsequent sensed events having morphologies that match the morphology of the first sensed event of the segment is greater than the second threshold ("YES" branch of block 172), control module 30 characterizes the segment as shockable (170) if the other gross and beat-based morphology analyses indicate shockable. This may occur, for example, when the tachyarrhythmia is a monomorphic VT. When control module 30 determines that the number of the subsequent sensed events having morphologies that match the morphology of the first sensed event of the tachyarrhythmia (or segment) is less than or equal to the second threshold ("NO" branch of block 172), control module 30 characterizes the tachyarrhythmia (or segment) as non-shockable regardless of whether the other gross and beat-based morphology analyses indicate shockable (174). This may occur, for example, when the detection of the tachyarrhythmia is likely a result of oversensing.

Various examples have been described. As described above, the concepts within this disclosure may be used in implanted systems that do not have an ICD. For example, in an implanted medical system have more than one leadless pacing device (e.g., a LPD in the atrium and an LPD in the ventricle), one or both of the leadless pacing devices may include perform pace detection, blanking, detection modifications, and the like. This may especially be the case for an LPD configured to detect VT/VF and provide ATP. These and other examples are within the scope of the following claims.

The invention claimed is:
1. An implantable medical device comprising:
  a sensing module configured to obtain an electrical signal produced by a patient's heart;
  a first pace pulse detector configured to analyze the sensed electrical signal to detect a first type of pulses having a first set of characteristics;
  a second pace pulse detector configured to analyze the sensed electrical signal to detect a second type of pulses having a second set of characteristics different than the first set of characteristics;
  one or more components configured to modify processing of the sensed electrical signal in response to detecting at least one of one of the first type of pulses or the second type of pulses;
  a control module configured to detect a heart rhythm that is shockable based on the modified processing of the sensed electrical signals; and
  a therapy module configured to deliver a shock to the patient's heart in response to detecting the heart rhythm is shockable.
2. The device of claim 1, wherein the first set of characteristics is a first amplitude and the first pace pulse detector includes a first threshold detector that detects the first type of pulses when an amplitude of the sensed electrical signal is greater than or equal to the first amplitude, and wherein the second set of characteristics is a second amplitude, the second amplitude being less than the first amplitude, and the second pace pulse detector includes a second threshold detector that detects the second type of pulses when the amplitude of the sensed electrical signal is greater than or equal to the second amplitude.

3. The device of claim 2, further comprising a third threshold detector that is configured to detect when the amplitude of the sensed electrical signal exceeds a third amplitude.

4. The device of claim 3, wherein the third amplitude is less than the second amplitude.

5. The device of claim 3, wherein the third amplitude is greater than the second amplitude and less than the first amplitude.

6. The device of claim 1, wherein the first type of pulses comprise pulses having amplitudes greater than or equal to 2-10 millivolts and the second type of pulses comprise pulses having amplitudes greater than or equal to one (1) millivolt.

7. The device of claim 6, wherein the first and second pulses have pulse widths of at least 1 millisecond.

8. The device of claim 1, further comprising:
a first quiet timer associated with the first pace pulse detectors, wherein, in response detection of the first type of pulse by the first pace pulse detector, the quiet timer prevents the first pace pulse detector from detecting another pulse for a first period of time; and
a second quiet timer associated with the second pace pulse detectors, wherein, in response detection of the second type of pulse by the second pace pulse detector, the quiet timer prevents the second pace pulse detector from detecting another pulse for a second period of time.

9. The device of claim 8, wherein the first and second period of time are at least thirty (30) milliseconds.

10. The device of claim 1, further comprising one or more noise detectors configured to obtain the sensed electrical signal, analyze the sensed electrical signal to detect noise, and activate an output to indicate the detection of noise in the sensed electrical signal.

11. The device of claim 1, wherein the first set of characteristics include at least one of a first amplitude, slew rate and/or pulse width and the first pace pulse detector detects the first type of pacing pulses when the amplitude, slew rate and/or pulse width of the sensed electrical signal satisfies the first set of characteristics, and wherein the second set of characteristics include at least one of a second amplitude, slew rate and/or pulse width and the second pace pulse detector detects the second type of pacing pulses when the amplitude, slew rate and/or pulse width of the sensed electrical signal satisfies the second set of characteristics.

12. The device of claim 1, wherein at least the first pace pulse detector is configured to obtain an input indicative of an over-range condition from at least one component processing the sensed electrical signals and detect the first type of pacing pulses when the input indicative of the over-range condition is active for a threshold period of time.

13. The device of claim 12, wherein obtaining the input indicative of an over-range condition from at least one component processing the sensed electrical signals comprises obtaining an input indicative of an over-range condition from one or more of an analog-to-digital converter (ADC) and a preamplifier.

14. The device of claim 13, wherein obtaining the input indicative of an over-range condition from one or more of the ADC and the preamplifier comprises obtaining one or more of an input over-range signal from the preamplifier, an input over-range signal from the ADC, and a slew rate over-range signal of the ADC.

15. The device of claim 1, further comprising:
a pace pulse detection module that includes the first and second pace pulse detectors, wherein the pace pulse detection module is configured to output one or more pace detect signals that indicate detection of the first and second types of pacing pulses; and
wherein the one or more components that obtain at least one of the one or more pace detect signals and modify processing of the sensed electrical signal in response to the pace detect signal indicating detection of the first or second type of pacing pulses.

16. The device of claim 15, wherein the one or more components includes:
a blanking control module that receives at least one of pace detect signals and activates a blanking control signal when the at least one of the pace detect signals indicates detection of the first type of pacing pulse; and
a blanking module that receives the blanking control signal and holds the sensed electrical signal at a current value when the blanking control signal is activated; and
a control module that receives at least one of pace detect signals and analyzes the at least one of the pace detect signals to determine whether to modify a tachyarrhythmia detection algorithm.

17. The device of claim 1, wherein the one or more components includes the control module, the control module being configured to modify processing of the sensed electrical signal by modifying a tachyarrhythmia detection algorithm based on the second type of pulses detected by the second pace pulse detector.

18. An extravascular implantable cardioverter-defibrillator (ICD) comprising:
a sensing module that obtains electrical signals sensed using at least an implantable electrical lead coupled to the ICD;
a pace detector including:
a first pace pulse detector that detects, within the obtained electrical signals, a first type of pulses having a first set of characteristics; and
a second pace pulse detector that detects, within the obtained electrical signals, a second type of pulses having a second set of characteristics different than the first set of characteristics;
a blanking module that holds the sensed electrical signal at a current value to remove the first type of pulse from the sensed electrical signal; and
a control module that modifies a tachyarrhythmia detection algorithm based on the detected pacing pulses.

19. The extravascular ICD of claim 18, wherein the control module is configured to detect a heart rhythm that is shockable based on the modified tachyarrhythmia detection algorithm, the ICD further comprising a therapy module configured to deliver a shock to the patient's heart in response to detecting the heart rhythm is shockable.

20. The device of claim 19, wherein the control module is further configured to:

detect an initiation of a pacing train in response to at least the second type of pulses detected by the second pace pulse detector;

determine that the pacing train is terminated based on the second type of pulses detected by the second pace pulse detector; and revert to an unmodified tachyarrhythmia detection algorithm in response to determining that the pacing train is terminated.

21. The device of claim 19, wherein the control module is configured to modify the tachyarrhythmia detection algorithm by at least modifying a morphology analysis of the sensed electrical signal.

* * * * *